US011771909B2

(12) United States Patent
Sullivan et al.

(10) Patent No.: US 11,771,909 B2
(45) Date of Patent: Oct. 3, 2023

(54) WEARABLE CARDIAC DEFIBRILLATOR SYSTEM AUTHENTICATING PERSON ACTUATING CANCEL SWITCH

(71) Applicant: WEST AFFUM HOLDINGS DAC, Dublin (IE)

(72) Inventors: Joseph L. Sullivan, Kirkland, WA (US); David Peter Finch, Bothell, WA (US); Phillip Dewey Foshee, Jr., Woodinville, WA (US); Isabelle Banville, Newcastle, WA (US); Richard C. Nova, Seattle, WA (US); Krystyna Szul, Seattle, WA (US); Daniel Finney, Woodinville, WA (US); Laura Marie Gustavson, Redmond, WA (US); Gregory T. Kavounas, Bellevue, WA (US)

(73) Assignee: WEST AFFUM HOLDINGS DAC, Dublin (IE)

( * ) Notice: Subject to any disclaimer, the term of this patent is extended or adjusted under 35 U.S.C. 154(b) by 357 days.

(21) Appl. No.: 16/588,262

(22) Filed: Sep. 30, 2019

(65) Prior Publication Data
US 2020/0023190 A1    Jan. 23, 2020

Related U.S. Application Data

(62) Division of application No. 15/838,747, filed on Dec. 12, 2017, now Pat. No. 10,426,964, which is a
(Continued)

(51) Int. Cl.
*A61N 1/39*    (2006.01)
*A61B 5/00*    (2006.01)
(Continued)

(52) U.S. Cl.
CPC ...... *A61N 1/37254* (2017.08); *A61B 5/02405* (2013.01); *A61B 5/053* (2013.01);
(Continued)

(58) Field of Classification Search
CPC .............. A61N 1/37254; A61N 1/3904; A61N 1/3925; A61N 1/3968; A61N 1/3975;
(Continued)

(56) References Cited

U.S. PATENT DOCUMENTS 3,724,355 A    4/1973  Unger
4,583,524 A    4/1986  Hutchins
(Continued)

FOREIGN PATENT DOCUMENTS

WO    1998039061 A2    9/1998
WO    2012064604 A1    5/2012

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Jounal, May 31, 2013, pp. 1-14, doi:10.1093/eurheartj/eht167, European Society of Cardiology.
(Continued)

*Primary Examiner* — Lindsey G Wehrheim
(74) *Attorney, Agent, or Firm* — Christensen O'Connor Johnson Kindness PLLC

(57) ABSTRACT

A wearable cardiac defibrillator ("WCD") system may include a support structure that a patient can wear, an energy storage module that can store an electrical charge, and a discharge circuit that can discharge the electrical charge through the patient so as to shock him or her, while the patient is wearing the support structure. Embodiments may actively take into account bystanders, both to protect them from an inadvertent shock, and also to enlist their help. In
(Continued)

SAMPLE COMPONENTS OF WEARABLE
CARDIAC DEFIBRILLATOR (WCD) SYSTEM some embodiments the WCD system includes a speaker system that transmits a sound designed to assist a bystander to perform CPR. Optionally CPR chest compressions received by the patient can be further detected, and feedback can be given. In embodiments, a WCD system may include a user interface that can be controlled to output CPR prompts tailored to a skill level of the bystander.

20 Claims, 22 Drawing Sheets

Related U.S. Application Data division of application No. 15/364,127, filed on Nov. 29, 2016, now Pat. No. 9,878,173, which is a division of application No. 15/097,554, filed on Apr. 13, 2016, now Pat. No. 9,539,436, which is a division of application No. 14/529,082, filed on Oct. 30, 2014, now Pat. No. 9,339,663.

(60) Provisional application No. 61/955,389, filed on Mar. 19, 2014.

(51) Int. Cl.
 A61B 5/11 (2006.01)
 A61N 1/372 (2006.01)
 A61B 5/053 (2021.01)
 A61B 5/024 (2006.01)

(52) U.S. Cl.
 CPC .............. A61B 5/11 (2013.01); A61B 5/4836 (2013.01); A61B 5/6801 (2013.01); A61B 5/742 (2013.01); A61B 5/7405 (2013.01); A61N 1/3904 (2017.08); A61N 1/3925 (2013.01); A61N 1/3968 (2013.01); A61N 1/3975 (2013.01); A61N 1/3987 (2013.01); A61N 1/3993 (2013.01); A61B 5/74 (2013.01); A61B 2560/0242 (2013.01); A61N 1/39 (2013.01); A61N 1/39044 (2017.08); A61N 1/39046 (2017.08)

(58) Field of Classification Search
 CPC .............. A61N 1/3987; A61N 1/3993; A61N 1/39044; A61N 1/39046; A61N 1/39; A61B 5/02405; A61B 5/053; A61B 5/11; A61B 5/4836; A61B 5/6801; A61B 5/7405; A61B 5/742; A61B 5/74; A61B 2560/0242
 See application file for complete search history.

(56) References Cited

U.S. PATENT DOCUMENTS

| | | | |
|---|---|---|---|
| 4,619,265 A | 10/1986 | Morgan et al. | |
| 4,928,690 A | 5/1990 | Heilman et al. | |
| 4,955,381 A | 9/1990 | Way et al. | |
| 5,078,134 A | 1/1992 | Heilman et al. | |
| 5,228,449 A | 7/1993 | Christ et al. | |
| 5,353,793 A | 10/1994 | Bornn | |
| RE34,800 E | 11/1994 | Hutchins | |
| 5,394,892 A | 3/1995 | Kenny | |
| 5,405,362 A | 4/1995 | Kramer et al. | |
| 5,474,574 A | 12/1995 | Payne et al. | |
| 5,662,690 A | 9/1997 | Cole et al. | |
| 5,741,306 A * | 4/1998 | Glegyak | A61N 1/3904 607/5 |
| 5,782,878 A | 7/1998 | Morgan et al. | |
| 5,792,204 A | 8/1998 | Snell | |
| 5,902,249 A | 5/1999 | Lysler | |
| 5,913,685 A | 6/1999 | Hutchins | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder | |
| 6,437,083 B1 | 7/2002 | Owen et al. | |
| 6,529,875 B1 | 3/2003 | Nakajima | |
| 6,546,285 B1 | 4/2003 | Owen et al. | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,559,902 B2 | 7/2009 | Ting et al. | |
| 7,865,238 B2 | 1/2011 | Brink | |
| 7,870,761 B2 | 1/2011 | Valentine et al. | |
| 7,974,689 B2 | 7/2011 | Volpe et al. | |
| 8,140,154 B2 | 10/2012 | Donnelly et al. | |
| 8,369,944 B2 | 2/2013 | Macho et al. | |
| 8,644,925 B2 | 2/2014 | Volpe et al. | |
| 8,676,313 B2 | 3/2014 | Volpe et al. | |
| 8,965,500 B2 | 2/2015 | Macho et al. | |
| 9,008,801 B2 | 4/2015 | Kaib et al. | |
| 9,131,901 B2 | 9/2015 | Volpe et al. | |
| 9,132,267 B2 | 9/2015 | Kaib | |
| 9,345,898 B2 | 5/2016 | Piha et al. | |
| 9,878,171 B2 | 1/2018 | Kaib | |
| 9,901,741 B2 | 2/2018 | Chapman et al. | |
| 10,016,613 B2 | 7/2018 | Kavounas | |
| 2002/0181680 A1 | 12/2002 | Linder et al. | |
| 2003/0158593 A1 | 8/2003 | Heilman et al. | |
| 2004/0030365 A1* | 2/2004 | Rubin | A61N 1/37282 607/60 |
| 2005/0107833 A1 | 5/2005 | Freeman et al. | |
| 2005/0107834 A1 | 5/2005 | Freeman et al. | |
| 2006/0173499 A1 | 8/2006 | Hampton et al. | |
| 2006/0270952 A1 | 11/2006 | Freeman et al. | |
| 2008/0306562 A1* | 12/2008 | Donnelly | A61N 1/0484 607/6 |
| 2008/0312709 A1* | 12/2008 | Volpe | A61B 5/339 607/6 |
| 2009/0005827 A1 | 1/2009 | Weintraub et al. | |
| 2009/0270930 A1* | 10/2009 | Walker | A61N 1/3904 607/5 |
| 2010/0007413 A1 | 1/2010 | Herleikson | |
| 2010/0298899 A1 | 11/2010 | Donnelly et al. | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0191476 A1 | 7/2012 | Reid et al. | |
| 2012/0265265 A1 | 10/2012 | Razavi et al. | |
| 2012/0283794 A1 | 11/2012 | Kaib et al. | |
| 2012/0302860 A1 | 11/2012 | Volpe et al. | |
| 2013/0085538 A1 | 4/2013 | Volpe et al. | |
| 2013/0144355 A1 | 6/2013 | Macho et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0012144 A1 | 1/2014 | Crone | |
| 2014/0025131 A1 | 1/2014 | Sullivan et al. | |
| 2014/0046391 A1 | 2/2014 | Cowan et al. | |
| 2014/0070957 A1 | 3/2014 | Longinotti-Burtonil et al. | |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2015/0148857 A1 | 5/2015 | Macho et al. | |
| 2016/0004831 A1 | 1/2016 | Carlson et al. | |
| 2016/0283900 A1 | 9/2016 | Johnson et al. | |
| 2017/0319862 A1 | 11/2017 | Foshee, Jr. et al. | |

(56) References Cited

U.S. PATENT DOCUMENTS

| | | |
|---|---|---|
| 2017/0367591 A1 | 12/2017 | Jorgenseon |
| 2018/0184933 A1 | 7/2018 | Sullivan et al. |
| 2018/0185662 A1 | 7/2018 | Foshee, Jr. et al. |
| 2018/0243578 A1 | 8/2018 | Volosin |
| 2019/0030352 A1 | 1/2019 | Sullivan et al. |
| 2019/0076666 A1 | 3/2019 | Medema |

OTHER PUBLICATIONS

Lifecor LifeVest System Model WCD 3100 Operator's Manual, 2006, PN 20B0040 Rev FI, Zoll Lifecor Corporation, Pittsburgh, PA.

Heartstart MRx and XL AED Algorithm—Application Note, Jul. 2001, Edition 2 Phillips Healthcare, USA.

Zoll LifeVest Model 4000 Patient Manual PN 20B0047 Rev B, (C) 2009-2012.

The LifeVest Network/Patient Data Management System, Zoll, 2015, 20C0503 Rev A.

\* cited by examiner

SAMPLE COMPONENTS OF WEARABLE CARDIAC DEFIBRILLATOR (WCD) SYSTEM

SAMPLE COMPONENTS OF EXTERNAL DEFIBRILLATOR

SAMPLE COMPONENTS OF WEARABLE CARDIAC DEFIBRILLATOR SYSTEM

*WCD SOUNDING IN PATIENT'S VOICE*

PULSELESS ELECTRICAL ACTIVITY
(P.E.A.) METHODS

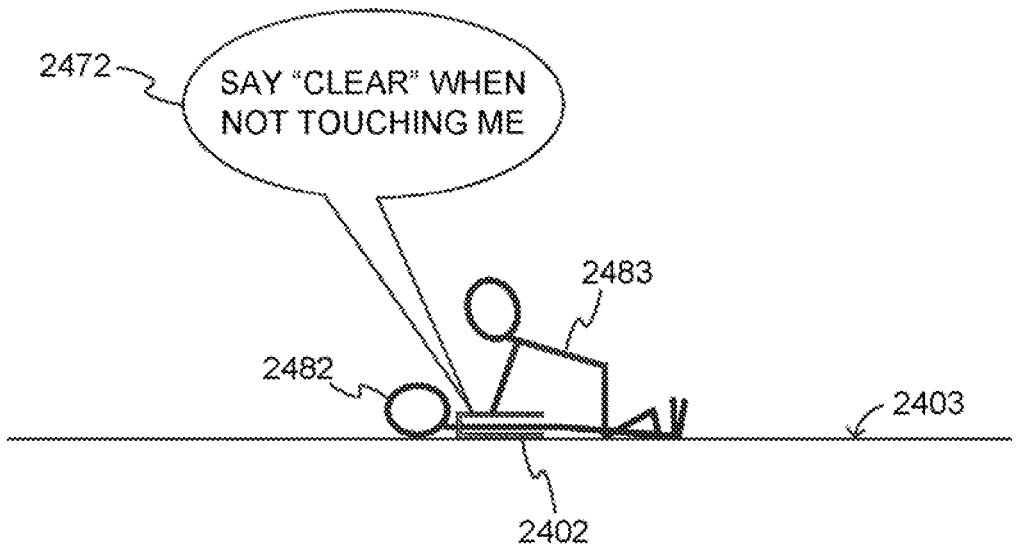
FIG. 24
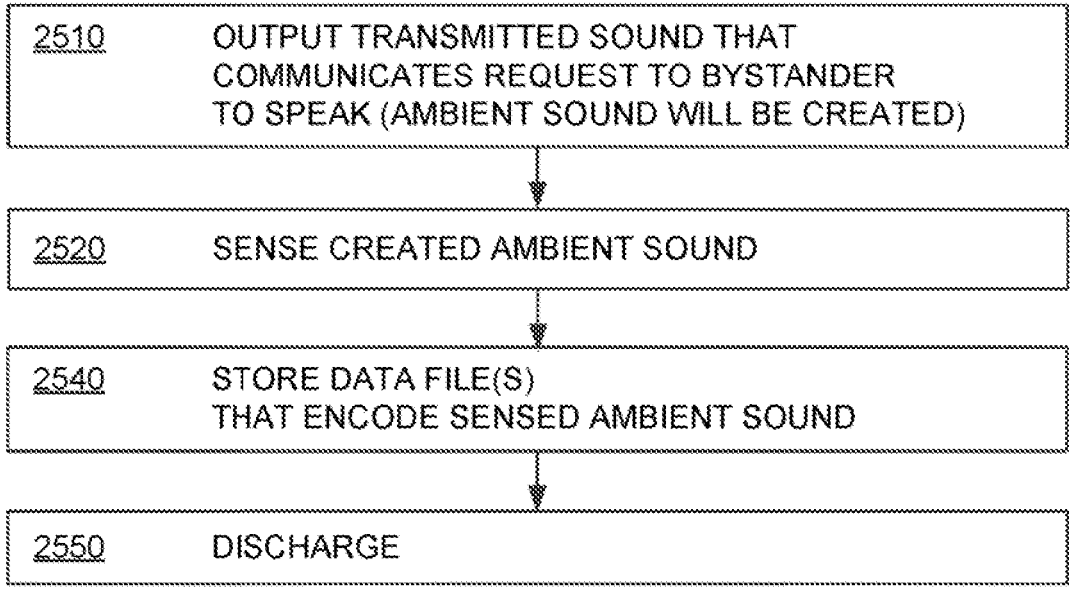
FIG. 25  METHODS

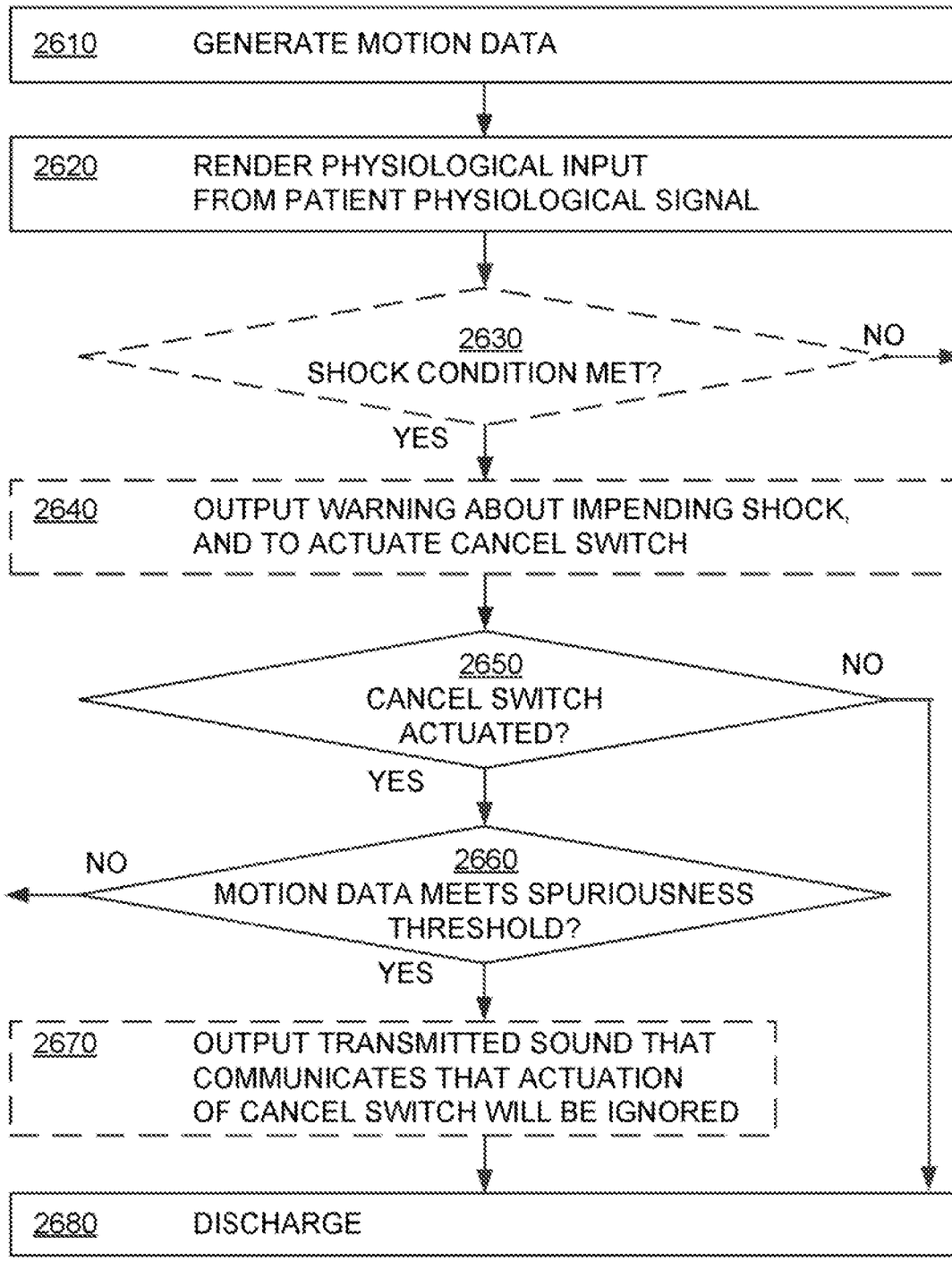
FIG. 26 METHODS

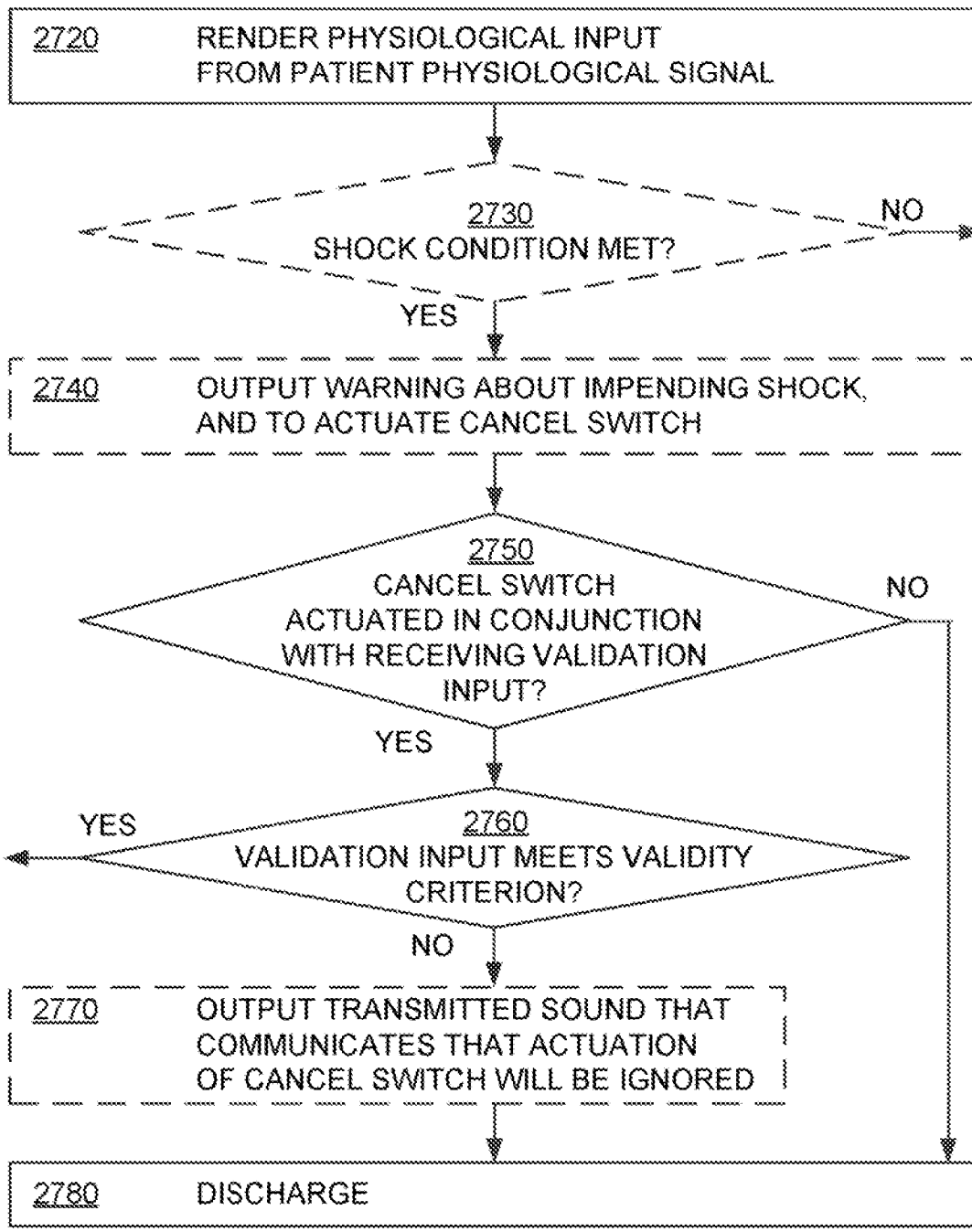
FIG. 27　　　*METHODS*

WEARABLE CARDIAC DEFIBRILLATOR SYSTEM AUTHENTICATING PERSON ACTUATING CANCEL SWITCH

CROSS REFERENCE TO RELATED PATENT APPLICATIONS

This patent application is a divisional of U.S. patent application Ser. No. 15/838,747 filed on Dec. 12, 2012, which in turn is a divisional of U.S. patent application Ser. No. 15/364,127 filed on Nov. 29, 2016 and issued as U.S. Pat. No. 9,878,173 issued on Jan. 30, 2018, which in turn is a divisional of U.S. patent application Ser. No. 15/097,554 filed on Apr. 13, 2016 and issued as U.S. Pat. No. 9,539,436 on Jan. 10, 2017, which in turn is a divisional of U.S. patent application Ser. No. 14/529,082 filed on Oct. 30, 2014 and issued as U.S. Pat. No. 9,399,663 B2 on May 17, 2016, which in turn claims priority from U.S. Provisional Patent Application Ser. No. 61/955,389, filed Mar. 19, 2014 and now expired, the disclosure of which is hereby incorporated by reference for all purposes.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim.

Some people have an increased risk of SCA. People at a higher risk include individuals who have had a heart attack, or a prior SCA episode. A frequent recommendation is for these people to receive an Implantable Cardioverter Defibrillator ("ICD"). The ICD is surgically implanted in the chest, and continuously monitors the person's electrocardiogram ("ECG"). If certain types of heart arrhythmias are detected, then the ICD delivers an electric shock through the heart.

After being identified as having an increased risk of an SCA, and before receiving an ICD, these people are sometimes given a wearable cardiac defibrillator ("WCD") system. A WCD system typically includes a harness, vest, or other garment for wearing by the patient. The system includes a defibrillator and external electrodes, which are attached on the inside of the harness, vest, or other garment. When a patient wears a WCD system, the external electrodes may then make good electrical contact with the patient's skin, and therefore can help monitor the patient's ECG. If a shockable heart arrhythmia is detected, then the defibrillator of the WCD system delivers the appropriate electric shock through the patient's body, and thus through the heart.

A wearable defibrillator system (WCD) system will typically be worn under the outer garments of a patient. If the patient collapses, a bystander might not help; even if they mean to help, they might not know about WCD systems, or what to do. A bystander trained in Cardio Pulmonary Resuscitations (CPR) might know to try to administer CPR chest compressions and ventilations; this intended rescuer, however, might not know that the patient is already wearing a WCD system, which could be further preparing to administer an electric shock through the patient, and which could be dangerous to whoever is touching the patient at the time.

BRIEF SUMMARY

The present description gives instances of wearable cardiac defibrillator ("WCD") systems, software, and methods, the use of which may help overcome problems and limitations of the prior art. A WCD system may include a support structure that a patient can wear, an energy storage module that can store an electrical charge, and a discharge circuit that can discharge the electrical charge through the patient so as to shock him or her, while the patient is wearing the support structure. Embodiments may actively take into account bystanders, both to protect them from an inadvertent shock, and also to enlist their help.

In embodiments, a WCD system may include a speaker system and a memory. Prompts may have been saved in advance in the patient's own voice, and stored in the memory. In case of an emergency, the prompts may be played by the speaker system in the patient's own voice, and heard by a bystander.

In embodiments, a WCD system may include a user interface or a capacitance meter. Upon sensing that the patient is being touched by a person other than the patient, the WCD system may prevent discharging the electrical charge, so as to protect an intended rescuer from being shocked.

In embodiments, a WCD system may include a proximity detector and a speaker system. Upon inferring that no bystander is nearby, the speaker system may transmit a sound at a higher intensity than otherwise, hoping to attract attention.

In embodiments, a WCD system may include a proximity detector and a speaker system. Upon inferring that a bystander is closer than a threshold, the speaker system may transmit a sound with a first content, as opposed to a sound with a second content. The first content could be instructing the bystander, while the second content could be requesting that a bystander who is hopefully close enough become engaged.

In embodiments, a WCD system may be able to detect whether the patient is suffering from Pulseless Electrical Activity (P.E.A.). In such embodiments, the WCD system may announce it, and possibly even discharge the charge through the patient anyway, as a last resort. A bystander's help may be requested and, if received, shocking might become not necessary.

In embodiments, a WCD system may include a speaker system, and request a bystander to place a mobile communication device close to the speaker system, sometimes after first dialing a specific telephone number. The speaker system may transmit sounds that communicate aspects of the patient and the event, and which may be thus received by a remote care center over a wireless communication link.

In embodiments, a WCD system may include a speaker system that transmits a sound, which has periodic contents that are designed to assist a bystander to perform CPR. Optionally CPR chest compressions are further detected, and feedback can be given. In embodiments, a WCD system may include a user interface that can differentiate among bystanders. The user interface may output CPR prompts that are tailored to a skill level of the bystander.

In embodiments, a WCD system may include a microphone. It might be ready to deliver a shock, but may not if it hears from a bystander a preset delaying word, such as "NO".

In embodiments, a WCD system may include a microphone. It might be ready to deliver a shock, but may first wait before doing so until it hears from a bystander a preset ready word, such as: "CLEAR".

In embodiments, a WCD system may include a speaker system that transmits a sound requesting a bystander to speak. The WCD system may include a microphone and a memory to sense what the bystander may say, and record it. The sensed speech may be even interpreted for operation.

In embodiments, a WCD system may include a cancel switch that can cancel an impending shock, and ways to determine whether the cancel switch has been actuated inappropriately, in which case the actuation may be ignored. A motion detector may generate motion data, and the actuation may be ignored if the motion data meets a spuriousness threshold.

In embodiments, a WCD system may include a cancel switch that can cancel an impending shock, and ways to prevent it from being actuated without prior authorization. The cancel switch can be configured to be actuated in conjunction with receiving a validation input, so as to authenticate the person who is actuating it. The validation input can be a code entered in a keyboard, or a fingerprint scanned in a fingerprint reader.

In embodiments, a WCD system may include a user interface, of which all or portions can be accessed by a bystander who can enter a correct validation input. The validation input can be a code entered in a keyboard, or a fingerprint scanned in a fingerprint reader.

Embodiments also include combinations of the above.

These and other features and advantages of this description will become more readily apparent from the Detailed Description, which proceeds with reference to the associated drawings in which:

BRIEF DESCRIPTION OF THE DRAWINGS

FIG. 24 is a diagram of a scene where a sample WCD system according to embodiments asks a bystander to speak.

FIG. 25 is a flowchart for illustrating sample methods according to embodiments.

FIG. 26 is a flowchart for illustrating sample methods according to embodiments.

FIG. 27 is a flowchart for illustrating sample methods according to embodiments.

DETAILED DESCRIPTION

As has been mentioned, the present description is about wearable cardiac defibrillator ("WCD") systems, software, and methods. Embodiments are now described in more detail.

A wearable cardiac defibrillator (WCD) system made according to embodiments has a number of components. These components can be provided separately as modules that can be interconnected, or can be combined with other components, etc.

A component of a WCD system can be a support structure, which is configured to be worn by the patient. The support structure can be any structure suitable for wearing, such as a harness, a vest, a half-vest—for example over the left side of the torso that positions electrodes on opposite sides of the heart, one or more belts that are configured to be worn horizontally or possibly vertically over a shoulder, another garment, and so on. The support structure can be implemented in a single component, or multiple components. For example, a support structure may have a top component resting on the shoulders, for ensuring that the defibrillation electrodes will be in the right place for defibrillating, and a bottom component resting on the hips, for carrying the bulk of the weight of the defibrillator. A single component embodiment could be with a belt around at least the torso. Other embodiments could use an adhesive structure or another way for attaching to the person, without encircling any part of the body. There can be other examples.

Figure 1:
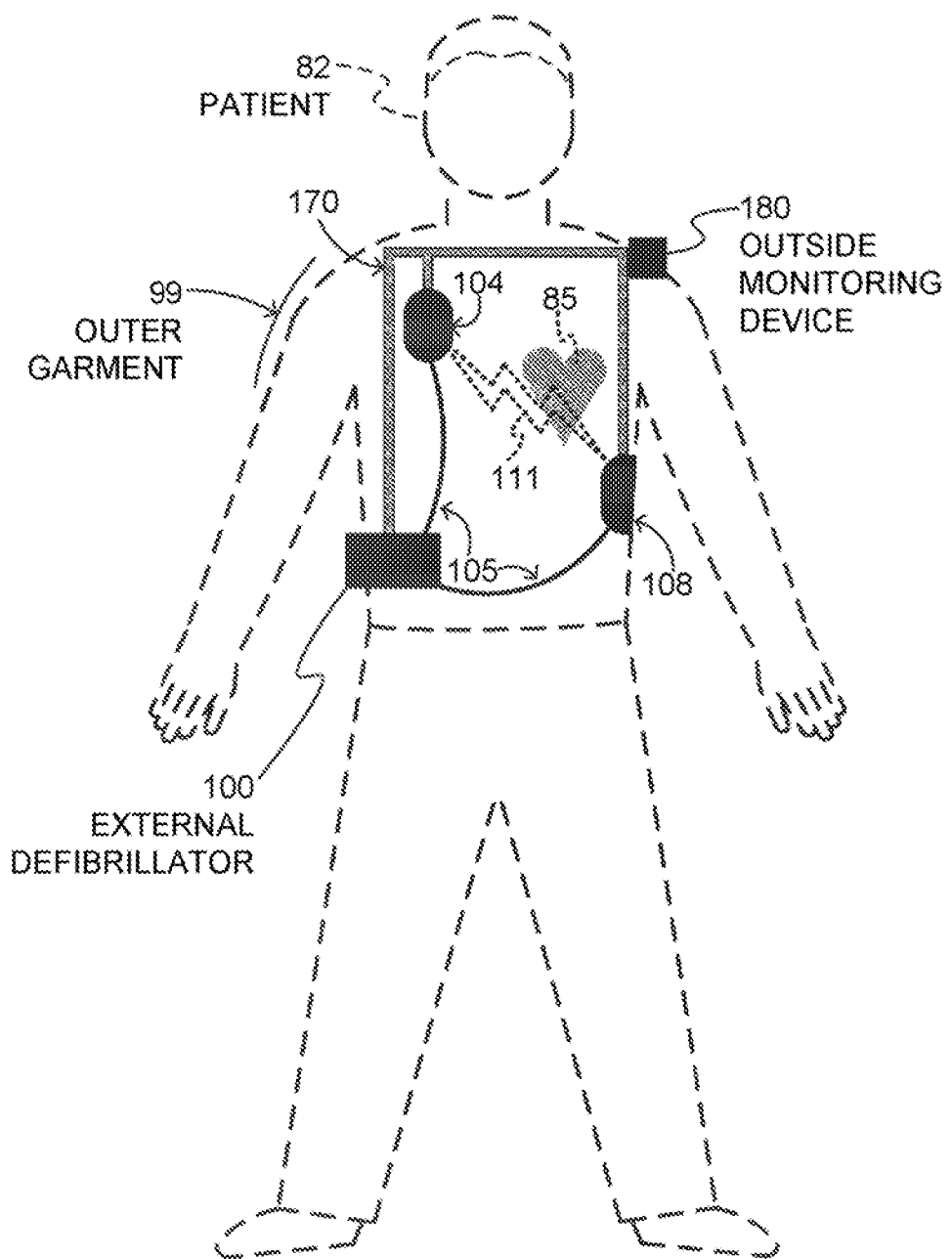
FIG. 1 is a diagram of components of a sample wearable cardiac defibrillator (WCD) system, made according to embodiments.

FIG. 1 depicts components of a WCD system made according to embodiments, as it might be worn by a person 82. A person such as person 82 may also be referred to as a patient and/or wearer, since that person wears components of the WCD system. Patient 82 may wear garments, one or more of which can be associated with a WCD system. In addition, a portion of an outer garment 99 is shown. Outer garment 99 might be obscuring the WCD system that patient 82 is wearing.

In FIG. 1, a generic support structure 170 is shown relative to the body of person 82, and thus also relative to his or her heart 85. Structure 170 could be a harness, a vest, a half-vest, one or more belts, or a garment, etc., as per the above. Structure 170 could be implemented in a single component, or multiple components, and so on. Structure 170 is wearable by person 82, but the manner of wearing it is not depicted, as structure 170 is depicted only generically in FIG. 1.

A wearable cardiac defibrillator (WCD) system is configured to defibrillate a patient who is wearing it, by delivering electrical charge to the patient's body in the form of an electric shock delivered in one or more pulses. FIG. 1 shows a sample external defibrillator 100, and sample defibrillation electrodes 104, 108, which are coupled to external defibrillator 100 via electrode leads 105. Defibrillator 100 and defibrillation electrodes 104, 108 are coupled to support structure 170. As such, many of the components of defibrillator 100 can be therefore coupled to support structure 170. When defibrillation electrodes 104, 108 make good electrical contact with the body of person 82, defibrillator 100 can administer, via electrodes 104, 108, a brief, strong electric pulse 111 through the body. Pulse 111, also known as a defibrillation shock or therapy shock, is intended to go through and restart heart 85, in an effort to save the life of person 82. Pulse 111 can further include one or more pacing pulses, and so on.

A prior art defibrillator typically decides whether to defibrillate or not based on an electrocardiogram ("ECG") signal of the patient. However, defibrillator 100 can defibrillate, or not defibrillate, also based on other inputs.

The WCD system may optionally include an outside monitoring device 180. Device 180 is called an "outside" device because it is provided as a standalone device, for example not within the housing of defibrillator 100. Device 180 can be configured to monitor at least one local parameter. A local parameter can be a parameter of patient 82, or a parameter of the WCD system, or a parameter of the environment, as will be described later in this document.

Optionally, device 180 is physically coupled to support structure 170. In addition, device 180 can be communicatively coupled with other components, which are coupled to support structure 170. Such communication can be by a communication module, as will be deemed applicable by a person skilled in the art in view of this disclosure.

Notwithstanding the complexity and sophistication of a WCD system, it should not be forgotten that it might all be covered under outer garment 99 of patient 82. Moreover, such systems are not common, at least today. Accordingly, if patient 82 is found unconscious by an untrained bystander, the bystander might reasonably think that patient 82 has fainted. Such a bystander might not reasonably suspect that this patient has suffered from a cardiac related ailment, and is wearing an active WCD system that can deliver an electric shock to patient 82, and thus also to anyone touching patient 82. Moreover, when a person has fainted, it is customary to assist them by opening their shirt, for assisting their breathing. Upon seeing a harness of WCD system snugly around the chest of person 82, a well-meaning bystander might surmise that this WCD is further constricting the breathing of person 82, and might further try to loosen it.

Figure 2:
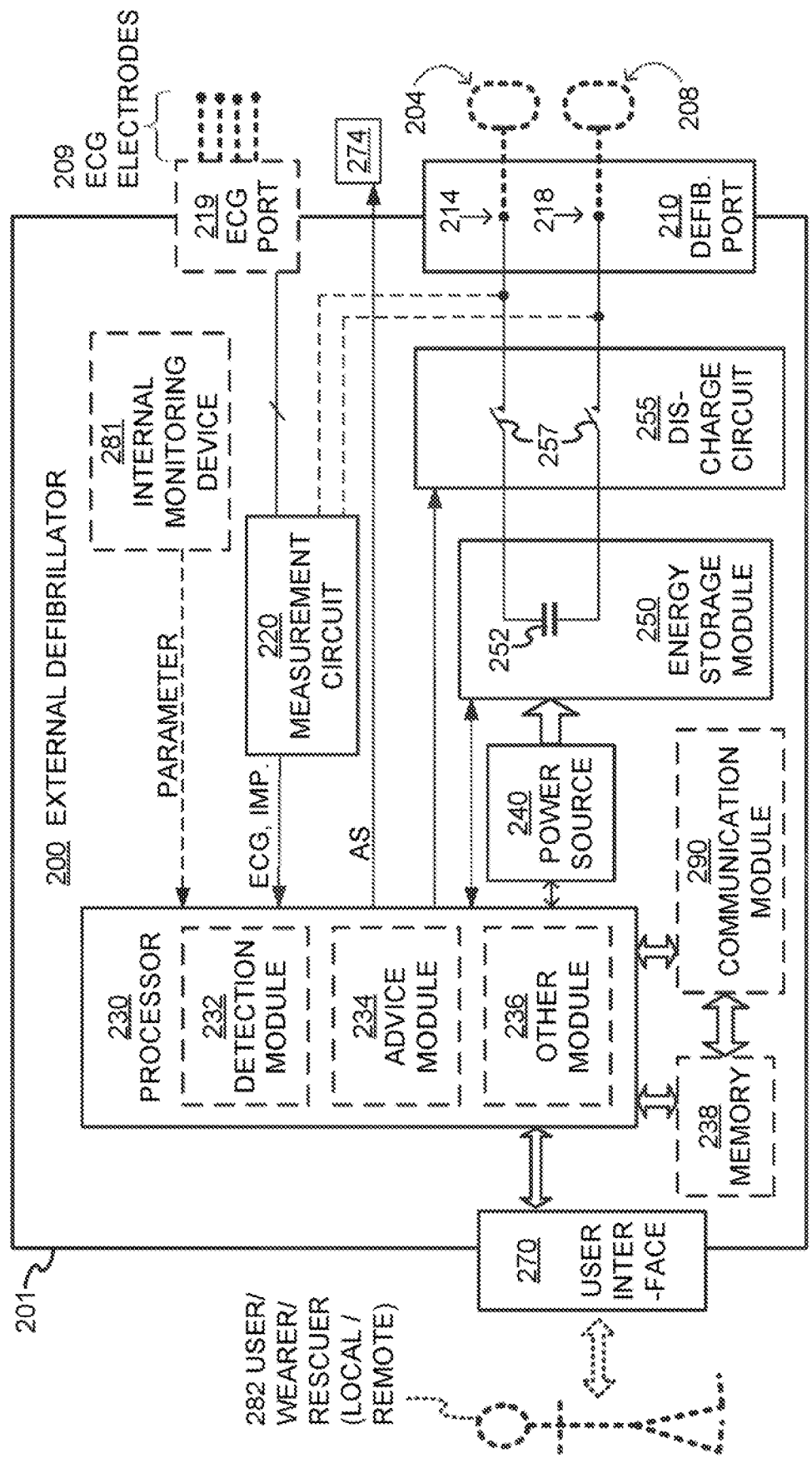
FIG. 2 is a diagram showing sample components of an external defibrillator, such as the one belonging in the WCD system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which is also known as casing 201.

External defibrillator 200 is intended for a patient who would be wearing it, such as person 82 of FIG. 1. Defibrillator 200 may further include a user interface 270 for a user 282. User 282 can be patient 82, also known as wearer 82. Or user 282 can be a local rescuer at the scene, such as a bystander who might offer assistance, or a trained person. Or, user 282 might be a remotely located trained caregiver in communication with the WCD system.

User interface 270 can be made in any number of ways. User interface 270 may include output devices, which can be visual, audible or tactile, for communicating to a user. For example, an output device can be a light, or a screen to display what is detected and measured, and provide visual feedback to rescuer 282 for their resuscitation attempts, and so on. Another output device can be a speaker, which can be configured to issue voice prompts, etc. Sounds, images, vibrations, and anything that can be perceived by user 282 can also be called human perceptible indications. User interface 270 may also include input devices for receiving inputs from users. Such input devices may include various controls, such as pushbuttons, keyboards, touchscreens, a microphone, validation input devices such as a keypad, a fingerprint reader, and so on. An input device can be a cancel switch, which is sometimes called a "live-man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can monitor patient parameters, patient physiological parameters, system parameters and/or environmental parameters, all of which can be called patient data. In other words, internal monitoring device 281 can be complementary or an alternative to outside monitoring device 180 of FIG. 1. Allocating which of the system parameters are to be monitored by which monitoring device can be done according to design considerations.

Patient physiological parameters include, for example, those physiological parameters that can be of any help in detecting by the WCD system whether the patient is in need of a shock, plus optionally their medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, the monitoring device could include a perfusion sensor, a pulse oximeter, a Doppler device for detecting blood flow, a cuff for detecting blood pressure, an optical sensor, illumination detectors and perhaps sources for detecting color change in tissue, a motion sensor, a device that can detect heart wall movement, a sound sensor, a device with a microphone, an $SpO_2$ sensor, and so on. Pulse detection is taught at least in Physio-Control's U.S. Pat. No. 8,135,462, which is hereby incorporated by reference in its entirety. In addition, a person skilled in the art may implement other ways of performing pulse detection.

In some embodiments, the local parameter is a trend that can be detected in a monitored physiological parameter of patient 82. A trend can be detected by comparing values of parameters at different times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$ or $CO_2$; f) respiratory function, respiratory rate, etc.; g) motion, level of activity; and so on. Once a trend is detected, it can be stored and/or reported via a communication link, along perhaps with a warning. From the report, a physician monitoring the progress of patient 82 will know about a condition that is either not improving or deteriorating.

Patient state parameters include recorded aspects of patient 82, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can about the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A wearable cardiac defibrillator (WCD) system made according to embodiments may include a motion detector. In embodiments, a motion detector can be implemented within monitoring device 180 or monitoring device 281. Such a motion detector can be configured to detect a motion event. In response, the motion detector may render or generate from the detected motion event a motion detection input that can be received by a subsequent device or functionality. A motion event can be defined as is convenient, for example a change in motion from a baseline motion or rest, etc. Such a motion detector can be made in many ways as is known in the art, for example by using an accelerometer.

System parameters of a WCD system can include system identification, battery status, system date and time, reports of self-testing, records of data entered, records of episodes and intervention, and so on.

Environmental parameters can include ambient temperature and pressure. A humidity sensor may provide information as to whether it is likely raining. Presumed patient location could also be considered an environmental parameter. The patient location could be presumed if monitoring device 180 or 281 includes a location sensor as per the above, such as a GPS location sensor.

Defibrillator 200 typically includes a defibrillation port 210, such as a socket in housing 201. Defibrillation port 210 includes electrical nodes 214, 218. Leads of defibrillation electrodes 204, 208, such as leads 105 of FIG. 1, can be plugged in defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in energy storage module 250. The electric charge will be the shock for defibrillation, pacing, and so on.

Defibrillator 200 may optionally also have an ECG port 219 in housing 201, for plugging in sensing electrodes 209, which are also known as ECG leads. It is also possible that sensing electrodes 209 can be connected continuously to ECG port 219, instead. Sensing electrodes 209 can help sense an ECG signal, e.g. a 12-lead signal, or a signal from a different number of leads, especially if they make good electrical contact with the body of the patient. Sensing electrodes 209 can be attached to the inside of support structure 170 for making good electrical contact with the patient, similarly as defibrillation electrodes 204, 208.

Defibrillator 200 also includes a measurement circuit 220. Measurement circuit 220 receives physiological signals of the patient from ECG port 219, if provided. Even if defibrillator 200 lacks ECG port 219, measurement circuit 220 can obtain physiological signals through nodes 214, 218 instead, when defibrillation electrodes 204, 208 are attached to the patient. In these cases, the patient's ECG signal can be sensed as a voltage difference between electrodes 204, 208. Plus, impedance between electrodes 204, 208 and/or the connections of ECG port 219 can be sensed. Sensing the impedance can be useful for detecting, among other things, whether these electrodes 204, 208 and/or sensing electrodes 209 are not making good electrical contact with the patient's body. These patient physiological signals can be sensed, when available. Measurement circuit 220 can then render or generate information about them as physiological inputs, data, other signals, etc. More strictly speaking, the information rendered by measurement circuit 220 is output from it, but this information can be called an input because it is received by a subsequent device or functionality as an input.

Defibrillator 200 also includes a processor 230. Processor 230 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 can be considered to have a number of modules. One such module can be a detection module 232. Detection module 232 can include a ventricular fibrillation ("VF") detector. The patient's sensed ECG from measurement circuit 220, which can be available as physiological inputs, data, or other signals, may be used by the VF detector to determine whether the patient is experiencing VF. Detecting VF is useful, because VF results in SCA. Detection module 232 can also include a ventricular tachycardia ("VT") detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more of ECG signals that are captured according to embodiments, and determining whether or not a shock criterion or shock condition is met. The determination can be made from a rhythm analysis of the captured ECG signal or otherwise.

In some embodiments, when the decision is to shock, an electrical charge is delivered to the patient. Delivering the electrical charge is also known as discharging. Shocking can be for defibrillation, pacing, and so on.

Processor 230 can include additional modules, such as other module 236, for other functions. In addition, if internal monitoring device 281 is indeed provided, it may be operated in part by processor 230, etc.

Defibrillator 200 optionally further includes a memory 238, which can work together with processor 230. Memory 238 may be implemented in any number of ways. Such ways include, by way of example and not of limitation, volatile memories, nonvolatile memories (NVM), read-only memories (ROM), random access memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read, and execute. More particularly, the programs can include sets of instructions in the form of code, which processor 230 may be able to execute upon reading. Executing is performed by physical manipulations of physical quantities, and may result in the functions, processes, actions and/or methods to be performed, and/or the processor to cause other devices or components or blocks to perform such functions, processes, actions and/or methods. The programs can be operational for the inherent needs of processor 230, and can also include protocols and ways that decisions can be made by advice module 234. In addition, memory 238 can store prompts for user 282, if they are a local rescuer. Moreover, memory 238 can store data. The data can include patient data, system data and environmental data, for example as learned by internal monitoring device 281 and outside monitoring device 180. The data can be stored in memory 238 before it is transmitted out of defibrillator 200, or stored there after it is received by it.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy storage capacitor, and so on. In some embodiments, power source 240 is controlled by processor 230.

Defibrillator 200 additionally includes an energy storage module 250, which can thus be coupled to the support structure of the wearable system. Module 250 is where some electrical energy is stored in the form of an electrical charge, when preparing it for sudden discharge to administer a shock. Module 250 can be charged from power source 240 to the right amount of energy, as controlled by processor 230. In typical implementations, module 250 includes a capacitor 252, which can be a single capacitor or a system of capacitors, and so on. As described above, capacitor 252 can store the energy in the form of electrical charge, for delivering to the patient.

Defibrillator 200 moreover includes a discharge circuit 255. When the decision is to shock, processor 230 can be configured to control discharge circuit 255 to discharge through the patient the electrical charge stored in energy storage module 250. When so controlled, circuit 255 can permit the energy stored in module 250 to be discharged to nodes 214, 218, and from there also to defibrillation electrodes 204, 208. Circuit 255 can include one or more switches 257. Switches 257 can be made in a number of ways, such as by an H-bridge, and so on. Circuit 255 can also be controlled via user interface 270.

Defibrillator 200 can optionally include a communication module 290, for establishing one or more wired or wireless communication links with other devices of other entities, such as a remote assistance center, Emergency Medical Services (EMS), and so on. Module 290 may also include an antenna, portions of a processor, and other sub-components as may be deemed necessary by a person skilled in the art. This way, data and commands can be communicated, such as patient data, event information, therapy attempted, CPR performance, system data, environmental data, and so on.

Defibrillator 200 can optionally include other components.

Returning to FIG. 1, in embodiments, one or more of the components of the shown WCD system have been customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. Such baseline physiological parameters can be used to customize the WCD system, in order to make its diagnoses more accurate, since bodies behave differently. For example, such parameters can be stored in a memory of the WCD system, and so on.

A programming interface can be made according to embodiments, which receives such measured baseline physiological parameters. Such a programming interface may input automatically in the WCD system the baseline physiological parameters, along with other data.

Figure 3:
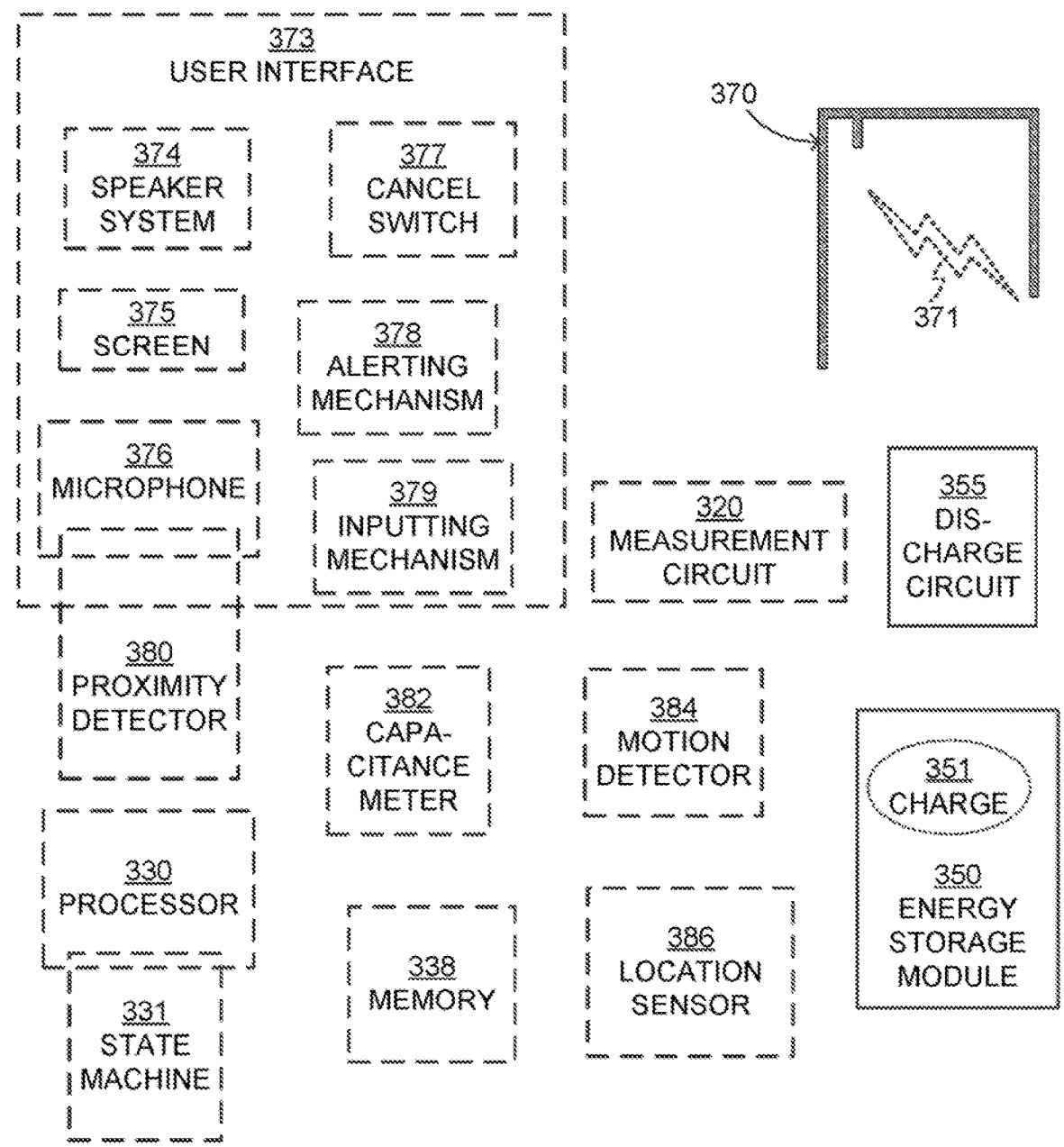
FIG. 3 is a diagram showing a collection of sample components of Wearable Cardiac Defibrillator systems included in many embodiments.

FIG. 3 is a diagram showing a collection 302 of sample components of Wearable Cardiac Defibrillator (WCD) systems, of which some are included in many of the embodiments described in this document. The components of collection 302 may be included as described here, and sometimes with further modification for the individual embodiments, as will be understood from the present description.

Collection 302 includes a support structure 370 that is configured to be worn by a patient, who is not shown. Support structure 370 is shown only generically in FIG. 3, and can be made as described for support structure 170. In addition, collection 302 includes an energy storage module 350, which can be configured to be coupled to support structure 370. Energy storage module 350 can be made as described for energy storage module 250, and can be configured to store an electrical charge 351. Moreover, collection 302 includes a discharge circuit 355, which can be configured to be coupled to energy storage module 350. Discharge circuit 355 can be made as described for discharge circuit 255, and can be configured to be coupled to energy storage module 350 and to discharge electrical charge 351 through the patient. Accordingly, discharge 371 may take place while support structure 370 is worn by the patient.

Collection 302 also includes a measurement circuit 320, a processor 330, and a memory 338, which can be made as described respectively for measurement circuit 220, processor 230, and memory 238. Measurement circuit 320 can be configured to render a physiological input from a patient physiological signal, such as an ECG. It can also be configured to render the patient impedance.

Processor 330 may control various components of a WCD system according to embodiments, even if not referred to explicitly. Moreover, processor 330 can be configured to determine from the physiological input of measurement circuit 320 whether or not a shock condition is met. If it is met, discharge circuit 355 can be configured to discharge electrical charge 351 through the patient. In addition, a state machine 331 may indicate an internal state of a WCD system, and may be implemented within processor 330, in conjunction with it, or otherwise, as is known.

Collection 302 additionally includes a user interface 373. In embodiments, user interface 373 can be made as described for user interface 270. In embodiments, user interface 373 may be configured to be coupled to support structure 370, in which case the components it includes can therefore be configured to be coupled to support structure 370. In embodiments, user interface 373 may include speaker system 374 that includes one or more speakers capable of outputting one or more transmitted sounds, a screen 375 that can be configured to display information, and a microphone 376 that can be configured to sense one or more ambient sounds. In embodiments, user interface 373 can be configured to input data files.

User interface 373 sometimes includes a cancel switch 377 for operations as described above. More particularly, cancel switch 377 can be configured to be actuated; and if it is actuated, it can prevent electrical charge 351 from being discharged, even if the shock condition is met. Cancel switch 377 can be implemented as a mechanical pushbutton, a switch, a button displayed on screen 375, a keypad into which a special code may be input, a fingerprint reader, and so on. When discharge 371 is imminent, the patient may be warned and be given a limited time to respond, in order to prove that discharge 371 is not necessary. This response can be made by actuating cancel switch 377.

User interface 373 sometimes includes an alerting mechanism 378. Alerting mechanism 378 can be configured to attract the attention of the patient when activated. Such can be useful when needing the patient to respond, for example for helping with a diagnosis. In some embodiments, alerting mechanism 378 is tactile, and can vibrate. In other embodiments, alerting mechanism 378 can be part of speaker system 374, and so on.

User interface 373 sometimes includes an inputting mechanism 379. This can be implemented by any of the mechanisms described for user interface 270, which permit a patient or a bystander to enter inputs that are also sometimes called usage inputs. In some embodiments, cancel switch 377 is an example of inputting mechanism 379.

Collection 302 further includes a capacitance meter 382, which can be configured to be coupled to support structure 370. Capacitance meter 382 may help indicate if the patient is being touched or released; in fact it is often good to indicate sudden changes in capacitance from events such as starting to touch and releasing.

Collection 302 further includes a motion detector 384 and a location sensor 386. Motion detector 384 can be thus configured to be coupled to the support structure, and to generate motion data. Location sensor 386 can be configured to be coupled to the support structure, and to detect a location of the support structure.

Collection 302 moreover includes a proximity detector 380. When provided, proximity detector 380 may be coupled to support structure 370. Proximity detector 380 may be configured to infer a proximity to support structure 370 of a person other than the patient, and who is not contacting the patient, such as a bystander.

Proximity detector 380 may be implemented in a number of ways. For example, it might be implemented using microphone 376. The inference can be made by judging from what microphone 376 senses, such as speech nearby, gradually changing intensity levels from the same source, and so on. Or, proximity detector 380 may be implemented by other components, such as an illumination detector, a thermal imager, or a camera, for receiving optical inputs. When such optical inputs change, they suggest that a bystander is nearby and likely moving around. A thermal imager might even work more discreetly, perhaps through a light outer garment. Or, proximity detector 380 may be implemented by a wireless signal receiver that needs to measure only signal intensity in common communication frequencies of mobile devices, such as 900 MHz in the US. When a bystander carrying a mobile communication device approaches, a wireless signal receiver may be able to notice a received signal of increased intensity, and accordingly make a better inference. Of course, such signals may change intensity according to other patterns, such as when the device receives or makes a call, but the time profiles of such intensity changes are more sudden and can be ruled out for not inferring a bystander approaching.

It is true that someone standing close could also be touching the patient. To rule out such bystanders who are also touching the patient, proximity detector 380 may also include a touch sensor. Such a touch sensor may be implemented by a motion detector 384, since motion of certain time profiles may indicate touching. In addition, a touch sensor may be implemented by capacitance meter 382 and/or user interface 373 as described above. When a touch sensor registers that the patient is being touched, proximity detector 380 can be on standby.

The above-mentioned components may be implemented in suitable places of a WCD system according to embodiments. Some of them can be implemented within monitoring device 180 or monitoring device 281.

The devices and/or systems mentioned in this document perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs.

In embodiments, a WCD system plays prompts in the patient's own prerecorded voice. An example is now described.

Figure 4:
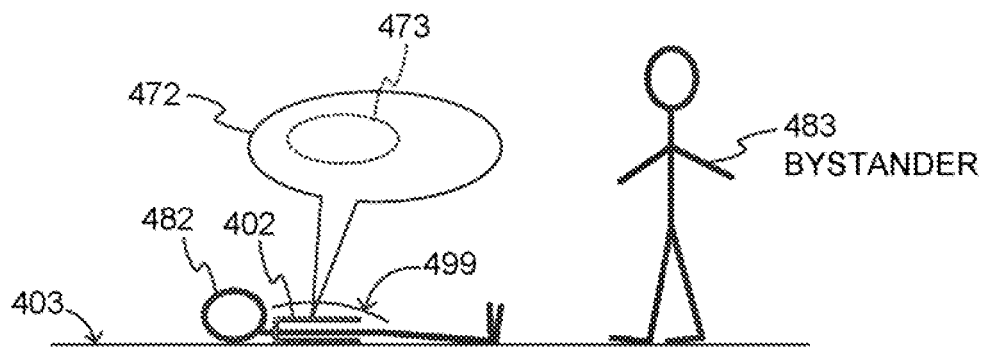
FIG. 4 is a diagram of a sample scene where a WCD system is used with a bystander, and which sounds in the patient's own voice according to embodiments.

FIG. 4 is a diagram of a scene where a patient 482 has fallen on ground 403, in an emergency. Patient 482 is wearing a WCD system 402, and an outer garment 499. A bystander 483 is nearby.

From collection 302 of FIG. 3, WCD system 402 may include processor 330, support structure 370, energy storage module 350, and discharge circuit 355. WCD system 402 may also include memory 338, which has been configured to store at least one data file (not shown) encoding a sound recorded in the voice of patient 482. It may also include speaker system 374, which has been configured to output a transmitted sound 472. Transmitted sound 472 includes a sound 473 that has been recorded in the voice of patient 482.

Transmitted sound 472 and sound 473 can be heard by bystander 483. Being in the voice of patient 482, sound 473 may have a better effect on bystander 483. Depending on the sounds, bystander 483 may be protected from electric shock, requested to help, and so on. For example, sound 472 or sound 473 can further communicate instructions, status information, a request to not touch the patient, a request to not remove the support structure from the patient, a request to say a preset word such as: "CLEAR" when not touching the patient but "NO" when touching, and so on.

In such embodiments, recording for sound 473 may take place in different ways, preferably during the fitting. In some embodiments, WCD system 402 may also include microphone 376, which has been configured to sense the voice of the patient during the fitting of the device. In such embodiments, the sensed voice becomes the recorded sound. In other embodiments, WCD system 402 may also include user interface 373, which has been configured to input the data file, and the inputted data file becomes stored in memory 338. In such a case, user interface 373 may operate as the aforementioned programming interface.

Transmitted sound 472 need not be only in the voice of the patient. For one example, sounds that speak to the patient when the patient is detected as alert can be in a voice different than his. Accordingly, memory 338 can be further configured to store another data file encoding another sound in a voice other than the voice of the patient. Transmitted sound 472 may further include the other sound.

Figure 5:
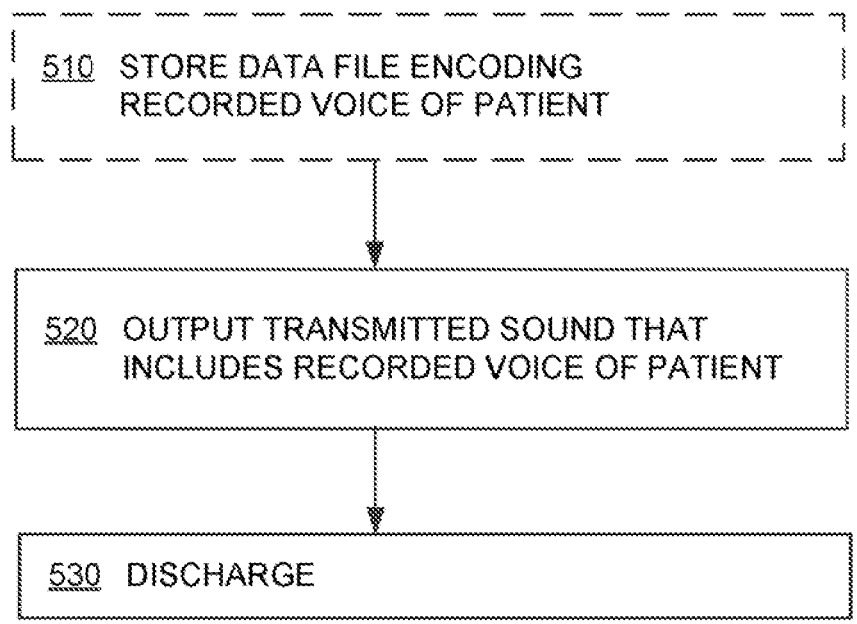
FIG. 5 is flowchart for illustrating sample methods according to embodiments.

A related method is now described. FIG. 5 is a flowchart 500, whose methods may be practiced by embodiments.

According to an optional operation 510, at least one data file is stored in a memory. The data file may encode a sound recorded in the voice of a patient. In embodiments where the WCD system includes a microphone, storing may be performed by sensing the patient's voice via the microphone and recording it. In embodiments where the WCD system includes a user interface, storing may be performed by inputting the data file via the user interface.

According to another operation 520, a transmitted sound is outputted. The transmitted sound may include the sound recorded in the voice of the patient. According to another operation 530, a discharge circuit may be controlled to discharge an electrical charge through a patient, while a support structure is worn by the patient.

In embodiments, a WCD system is capable of sensing may sense that the patient is being touched by a bystander, i.e. a person other than the patient. In such cases, the WCD system may prevent discharging of the electrical charge, so as to protect the other person, who is likely an intended rescuer. Sensing that the patient is being touched may be accomplished in a number of ways, and two examples are now described.

In a particular embodiment, from collection 302 of FIG. 3, a WCD system (not shown separately) may include processor 330, support structure 370, energy storage module 350, and discharge circuit 355.

Such a WCD system may also include capacitance meter 382, which can be coupled to the support structure. Capacitance meter 382 can be configured to detect whether or not the patient is being touched by a person other than the patient, for example while the support structure is worn by the patient. The discharge circuit can be prevented from discharging the electrical charge through the patient, while the capacitance meter detects that the patient is being touched by the person.

In another particular embodiment, from collection 302 of FIG. 3, a WCD system (not shown separately) may include processor 330, support structure 370, energy storage module 350, and discharge circuit 355. Such a WCD system may also include user interface 373 that is coupled to the support structure, and configured to receive a usage input by a person other than the patient. The discharge circuit can be prevented from discharging the electrical charge through the patient, while the user interface is receiving the usage input.

In embodiments, a WCD system may include a proximity detector and a speaker system. Upon inferring that no bystander is nearby, the speaker system may sound louder, i.e. may transmit a sound at a higher intensity than otherwise, hoping to attract attention. Examples are now described.

Figure 6:
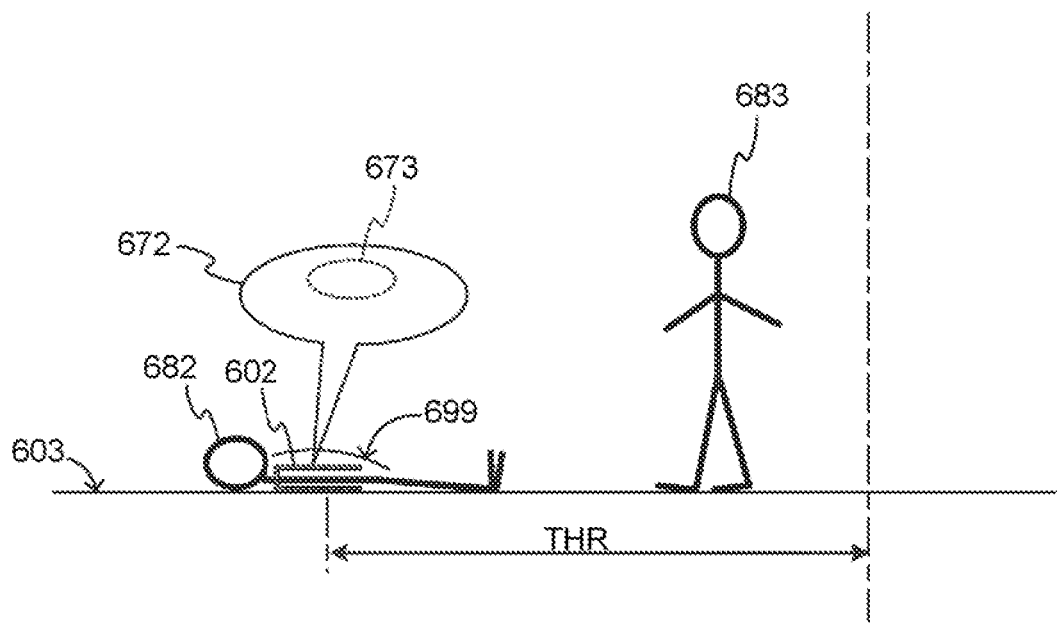
FIGS. 6 and 7 are diagrams of sample scenes for illustrating different modes of operation of an embodiment.
Figure 7:
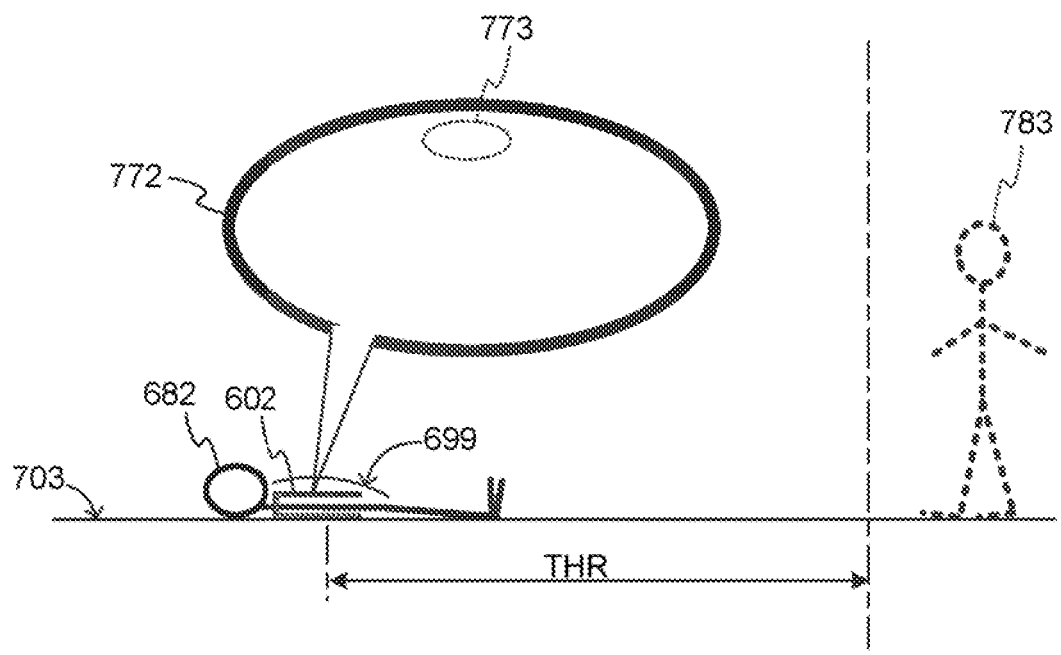

FIGS. 6 and 7 are diagrams of scenes for illustrating different modes of operation of an embodiment. Focusing first on FIG. 6, a scene is shown where a patient 682 has fallen on ground 603, in an emergency. Patient 682 is wearing a WCD system 602, and an outer garment 699. A bystander 683 is nearby, but not touching patient 682.

From collection 302 of FIG. 3, WCD system 602 may include processor 330, support structure 370, energy storage module 350, discharge circuit 355, and proximity detector 380. In the example of FIG. 6, the inferred proximity of a bystander 683 to support structure 602 is closer than a threshold. This is illustrated conceptually in FIG. 6, by showing bystander 683 as being within a physical range THR, but it should be remembered that the threshold need not be defined only in terms of direct distance or range. A bystander could be close in terms of direct distance, but around a corner. Rather, the threshold could be instead computational, and derived by having one or more of the implementations of proximity detector 380 "vote" as to whether they individually determine that a bystander is detected to be nearby, and then accounting for what the available votes reveal about a suitably chosen threshold. Such implementations include one or more of a microphone, an illumination detector, a thermal imager, a camera, a wireless signal receiver, a touch sensor to exclude those contacting, and so on.

WCD system 602 may also include speaker system 374, which has been configured to output a transmitted sound 672 that has a first intensity, since the inferred proximity is closer than the threshold. The first intensity can be preferably made appropriate to the inferred proximity or distance of bystander 683.

FIG. 7 shows a somewhat different scenario. Patient 682 has fallen on ground 703, in an emergency. Patient 682 is again wearing WCD system 602, and outer garment 699. In the example of FIG. 7, no bystander is necessarily detected nearby. In other words, the inferred proximity of a bystander 783 to support structure 602 is farther than the threshold, shown by being outside range THR. In fact, bystander 783 might not even be where shown, which is why bystander 783 is shown in dotted lines. In that case, speaker system 374 has been configured to output a transmitted sound 772 that has a second intensity that is larger than the first intensity—in other words is louder. The second intensity can be made appropriate for hailing someone, in the hope that bystander 783 is actually where shown, and their attention can be attracted.

In WCD system 602, therefore, if it is determined that the inferred proximity has changed, an intensity of the transmitted sound can be adjusted accordingly, automatically. For example, the scene of FIG. 6 may occur shortly after the scene of FIG. 7.

In some embodiments, the speaker system of WCD system 602 has a manual volume setting that is configured to adjust an intensity of the transmitted sounds. The manual volume setting can be adjustable by bystander 683, i.e. a person who is not the patient. So, if bystander 783 is actually where shown, his attention is indeed attracted, and he indeed comes nearby, he can adjust the intensity of subsequently transmitted sounds.

Transmitted sound 672 includes a content 673, and transmitted sound 772 includes a content 773. Contents 772, 773 stand for what is "said", if anything, during their respective sounds. Accordingly, contents 772, 773 can be the sounds of a siren, a buzzer, words, prompts, and so on. Contents 772, 773 may be the same (e.g. the words: "HELP ME"), or different. In some embodiments they are different depending on whether or not the inferred proximity is closer than the threshold.

Figure 8:
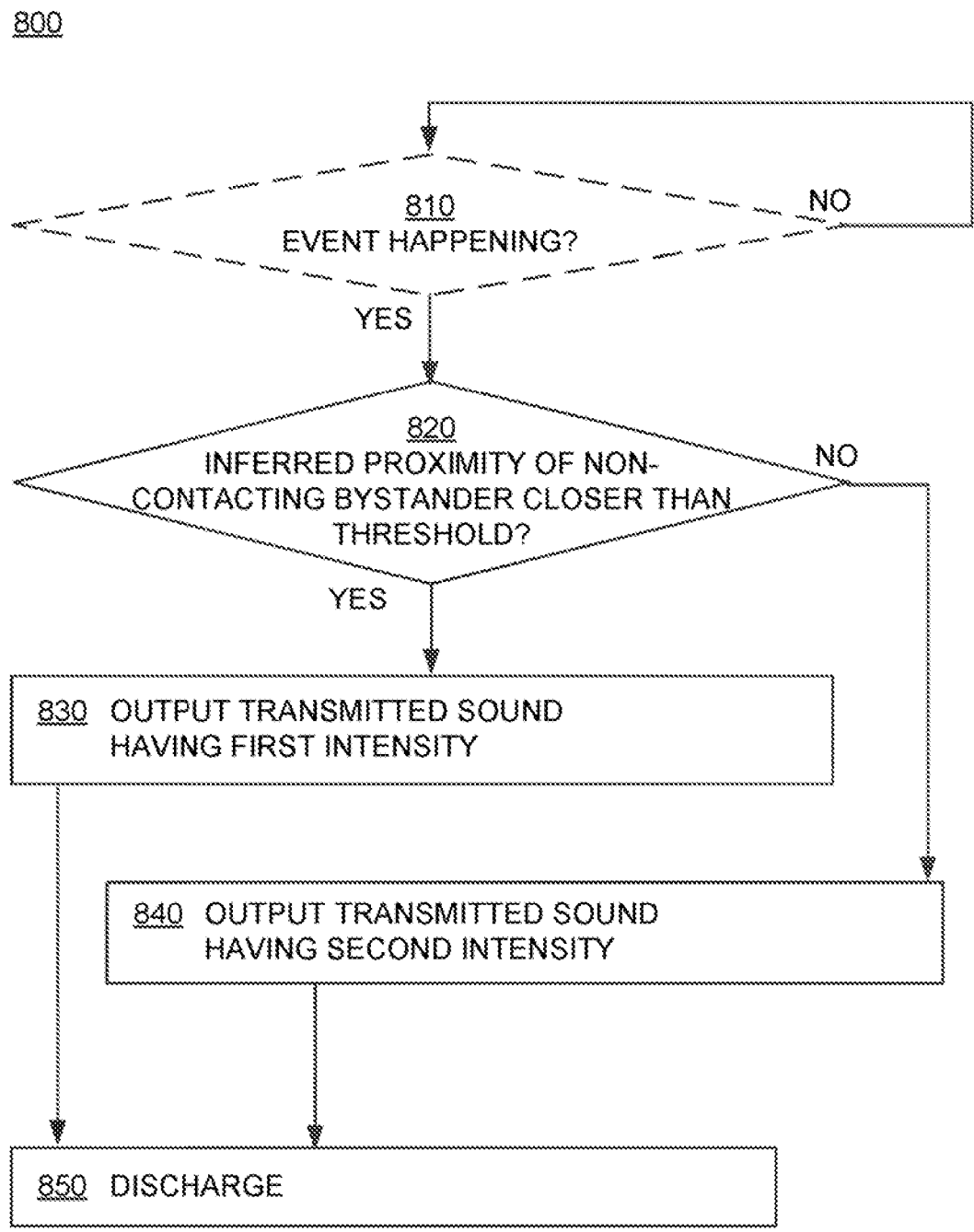
FIG. 8 is a flowchart for illustrating sample methods according to embodiments.

FIG. 8 shows a flowchart 800 for describing methods according to embodiments, which may also be practiced by WCD system 602 and other described embodiments.

According to an operation 810, it is determined whether or not an event of interest to WCD system 602 is taking place, such as the emergency event of FIGS. 6 and 7. While such an event is not taking place, execution may circulate to other operations, and then operation 810 may be repeated.

If at operation 810 the answer is yes, then according to another operation 820, a proximity is inferred to the support structure of WCD system 602 of a person other than the patient. Preferably the proximity is of a person who is not contacting the patient wearing WCD system 602. Then it is inquired whether or not the inferred proximity is closer than a threshold.

If the proximity is indeed closer than the threshold, it means that the bystander is closer and, according to another operation 830, a transmitted sound is output that has a first intensity. Otherwise the bystander is farther and, according to another operation 840, a transmitted sound is output that has a second intensity that is larger than the first intensity.

According to another operation 850, a discharge circuit is controlled to discharge an electrical charge through the patient, while the support structure is worn by the patient.

In addition, other operations are possible. For example, a manual volume adjustment input maybe received, and an intensity of the transmitted sound may be adjusted responsive to the received manual volume adjustment input.

In embodiments, a WCD system may address differently nearby bystanders than those farther away. Upon inferring that a bystander is closer than a threshold, the speaker system may transmit a sound with a first content, as opposed to a sound with a second content. Examples are now described.

Figure 9:
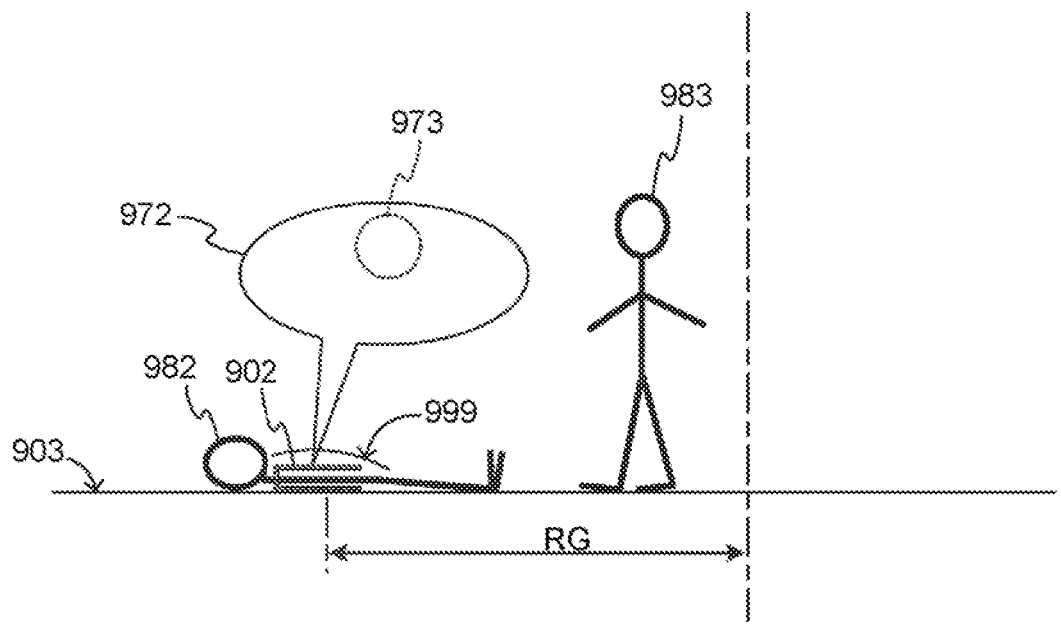
FIGS. 9 and 10 are diagrams of sample scenes for illustrating different modes of operation of an embodiment.
Figure 10:
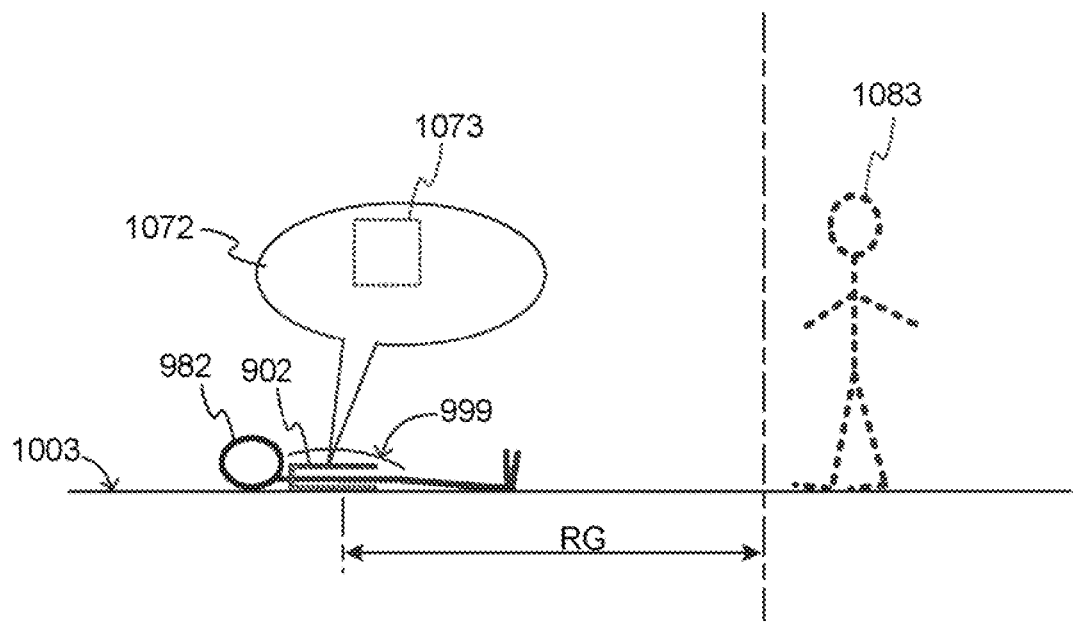

FIGS. 9 and 10 are diagrams of scenes for illustrating different modes of operation of an embodiment. Focusing first on FIG. 9, a scene is shown where a patient 982 has fallen on ground 903, in an emergency. Patient 982 is wearing a WCD system 902, and an outer garment 999. A bystander 983 is nearby, but not touching patient 982.

From collection 302 of FIG. 3, WCD system 902 may include processor 330, support structure 370, energy storage module 350, discharge circuit 355, and proximity detector 380. In the example of FIG. 9, the inferred proximity of a bystander 983 to support structure 902 is closer than a threshold RG. Threshold RG could be the same or different than threshold THR of FIGS. 6 and 7.

WCD system 902 may also include speaker system 374, which has been configured to output a transmitted sound 972 that has a first content 973, since the inferred proximity is closer than the threshold. First content 973 can be preferably made appropriate to the probable mental state of bystander 983, such as explaining in detail, guiding them and so on.

FIG. 10 shows a somewhat different scenario. Patient 982 has fallen on ground 1003, in an emergency. Patient 982 is again wearing WCD system 902, and outer garment 999. In the example of FIG. 10, no bystander is necessarily detected nearby. In other words, the inferred proximity of a bystander 1083 to support structure 902 is farther than the threshold. In fact, bystander 1083 might not even be where shown, which is why bystander 1083 is shown in dotted lines. In that case, speaker system 374 has been configured to output a transmitted sound 1072 that has a second content 1073 that is different from first content 973. The difference between first content 973 and second content 1073 is depicted by using different shapes in FIGS. 9, 10. Second content 1073 can be made appropriate for trying to engage someone who hopefully might be there.

In embodiments of WCD system 902, if it is determined that the inferred proximity has changed, an intensity of the transmitted sound can be adjusted accordingly, automatically. For example, the scene of FIG. 9 may occur shortly after the scene of FIG. 10.

In some embodiments, the speaker system of WCD system 902 has a manual volume setting that is configured to adjust an intensity of the transmitted sounds. The manual volume setting can be adjustable by bystander 983, i.e. a person who is not the patient.

In some embodiments, WCD system 902 also includes memory 338, which has been configured to store one or more data files that encode a first prompt and a second prompt. In such embodiments, the transmitted sound may communicate the first prompt as the first content, and the second prompt as the second content.

Figure 11:
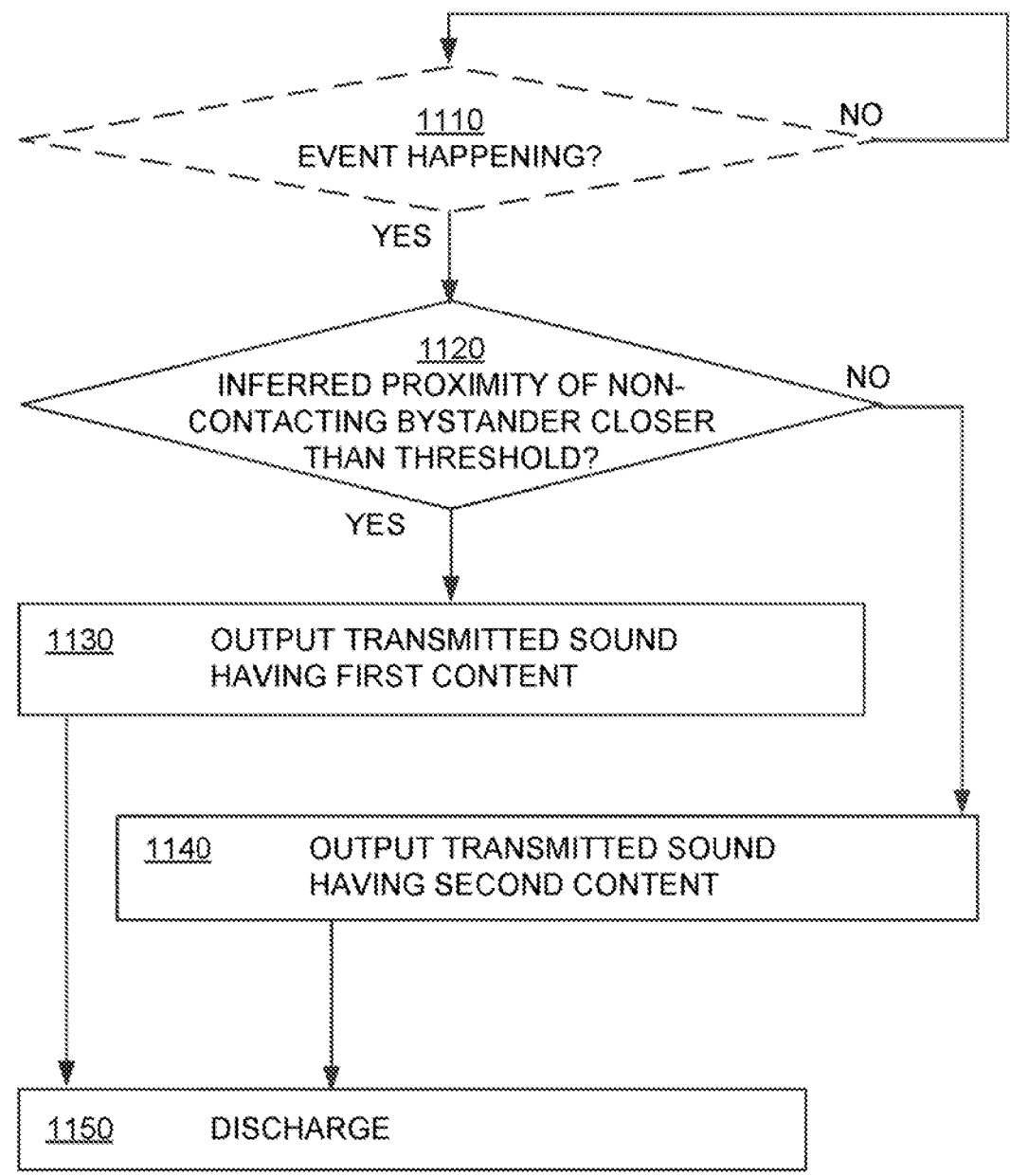
FIG. 11 is a flowchart for illustrating sample methods according to embodiments.

FIG. 11 shows a flowchart 1100 for describing methods according to embodiments, which may also be practiced by WCD system 902.

According to an operation 1110, it is determined whether or not an event of interest to WCD system 902 is taking place, such as the emergency event of FIGS. 9 and 10. While it does not, execution may circulate to other operations, and then operation 1110 may be repeated.

If at operation 1110 the answer is yes, then according to another operation 1120, a proximity of a person other than the patient to the support structure of WCD system 902 is inferred. Preferably the proximity is of a person who is not contacting the patient wearing WCD system 902. Then it is inquired whether or not the inferred proximity is closer than a threshold.

If the proximity is closer than the threshold, then according to another operation 1130, a transmitted sound is output that has a first content. Otherwise, according to another operation 1140, a transmitted sound is output that has a second content that is different from the first content. Again, optionally one or more data files could encode prompts that are communicated by the transmitted sound as the first content and the second content.

According to another operation 1150, a discharge circuit is then controlled to discharge an electrical charge through the patient, while the support structure is worn by the patient.

In addition, other operations are possible. For example, a manual volume adjustment input maybe received, and an intensity of the transmitted sound may be adjusted responsive to the received manual volume adjustment input.

In embodiments, a WCD system may be able to detect whether the patient is suffering from Pulseless Electrical Activity (P.E.A.). Examples are now described.

Figure 12:
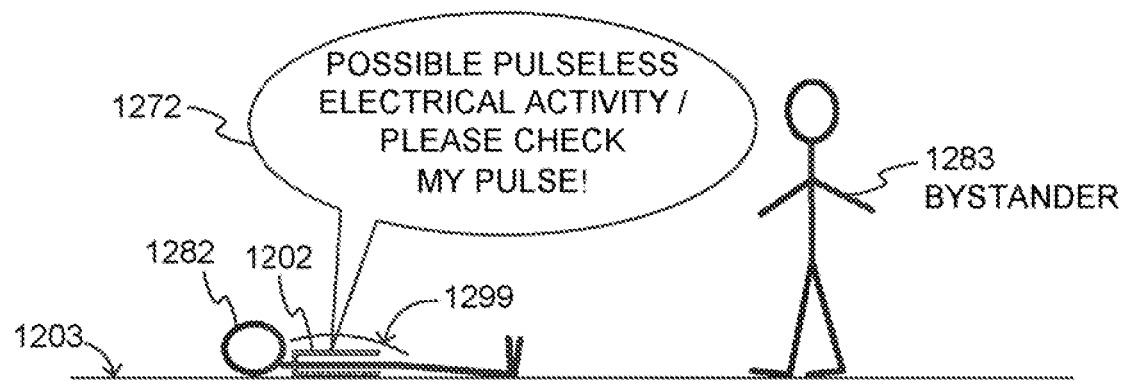
FIG. 12 is a diagram of a sample scene where a patient who could be suffering from Pulseless Electrical Activity is wearing a WCD system that is made according to embodiments.

FIG. 12 is a diagram of a scene where a patient 1282 has fallen on ground 1203, in an emergency that could be P.E.A. Patient 1282 is wearing a WCD system 1202 and an outer garment 1299. A bystander 1283 might be nearby, without touching patient 1282.

From collection 302 of FIG. 3, WCD system 1202 may include support structure 370, energy storage module 350, discharge circuit 355, measurement circuit 320 and processor 330. Processor 330 can be configured to determine from the physiological input of measurement circuit 320 whether the patient physiological signal rendered by measurement circuit 320 indicates that the patient could be suffering from Pulseless Electrical Activity (P.E.A.).

In some embodiments, the indication of P.E.A. can be bolstered by additional functionality. WCD system 1202 also includes motion detector 384 coupled to support structure 370. In these embodiments, it can be determined that the patient could be suffering from P.E.A. also from a motion detector signal generated by motion detector 384. For example, if the motion detector signal indicates that the patient is not moving at all while still having a sinus rhythm, the cause could be P.E.A. The chances of the ailment being P.E.A. can increase if previously there was regular motion, which has stopped abruptly. In addition, mechanical signs of circulation can be checked, for example as suggested in Physio-Control's US Patent Application 20060173499, published Aug. 3, 2006.

Before determining that the ailment is P.E.A. with high certainty, WCD system 1202 may try to receive confirmation from the patient. For example, in some embodiments WCD system 1202 also includes alerting mechanism 378 and inputting mechanism 379 of collection 302. Alerting mechanism 378 may be activated responsive to determining that the patient could be suffering from P.E.A. Alerting mechanism 378 could operate by voice, by a vibration, and so on. A time limit might be given to patient 1282 to respond, such as by making an entry in inputting mechanism 379. In embodiments where inputting mechanism 379 is implemented by cancel switch 377, making an entry would be by actuating cancel switch 377.

Before determining that the ailment is P.E.A. with high certainty, WCD system 1202 may also try to engage bystander 1283 for help. Accordingly, WCD system 1202 may further include speaker system 374 coupled to support structure 370. In these embodiments speaker system 374 can be configured to output a transmitted sound 1272 that communicates a request to check a pulse of the patient, includes the words: "Pulseless Electrical Activity" or the initials: "P.E.A.", or both.

If bystander 1283 indeed becomes engaged, perhaps no shock will be necessary. Perhaps bystander 1283 will follow the instructions, call for help, check the pulse, enter data in a user interface, perform CPR, and so on. In such instances, more can be done with transmitted sound 1272. For example, transmitted sound 1272 can include a transmitted sound having substantially periodic contents, which can be designed to assist a bystander to perform CPR chest compressions on the patient while the support structure is worn by the patient—in other words a metronome-type sound. Additionally, transmitted sound 1272 can communicate a request to not remove the support structure from the patient, or to say a delaying word such "NO" or "WAIT" if the patient is still touched, or to say a ready word such as "CLEAR", "YES", or "ALL CLEAR", after CPR is done and the patient is no longer touched. If all goes well, shocking as a last resort might not be necessary.

In some embodiments, if it is determined that the ailment is P.E.A. with some certainty, and in the event that no bystander is engaging, processor 330 can control discharge circuit 355 to discharge its electrical charge through the patient. The charge can be small, such as for pacing, or large such as for defibrillation. Either way, WCD system 1202 may thus discharge as a last resort. Indeed, if no better therapy is available, the discharge might restore the patient's sinus rhythm or change their rhythm to one that can be restored by further shocking. Again, in such cases, discharge circuit 355 can be controlled to discharge only if no entry is received in inputting mechanism 379, responsive to alerting mechanism 378 being activated.

Figure 13:
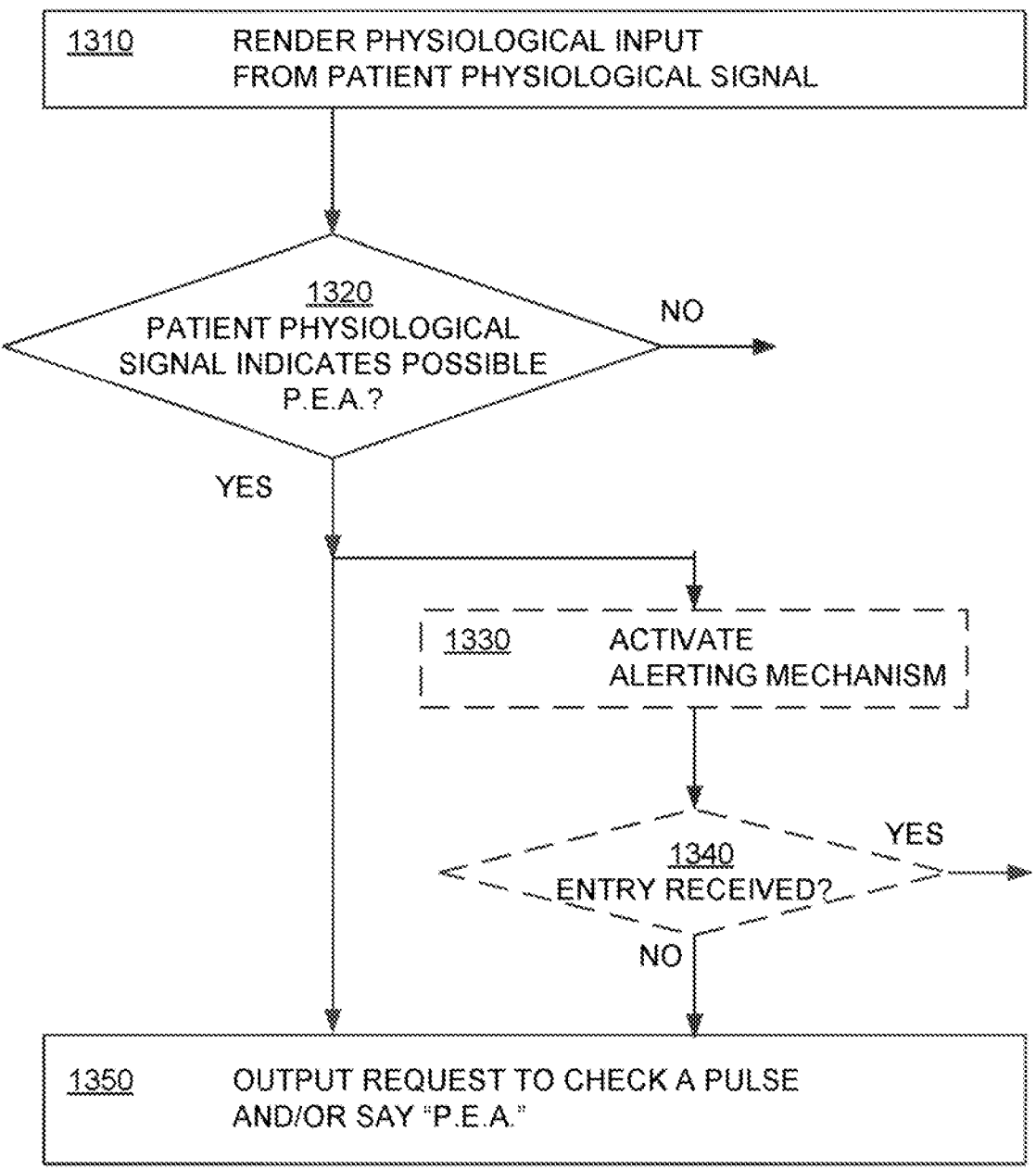
FIG. 13 is a flowchart for illustrating sample P.E.A. methods according to embodiments.

FIG. 13 shows a flowchart 1300 for describing P.E.A. methods according to embodiments. The methods of flowchart 1300 may also be practiced by WCD system 1202 and other embodiments described in this document.

According to an operation 1310, a physiological input may be rendered, for example by the measurement circuit. The physiological input may be rendered from a patient physiological signal.

According to another operation 1320, it is determined from the physiological input whether the patient physiological signal indicates that the patient could possibly be suffering from Pulseless Electrical Activity (P.E.A.). This determination need not be absolute—it can be a level of confidence. If not, which means that the level of confidence is less than a suitable threshold, then flowchart 1300 may be exited. In some embodiments, the WCD system further includes a motion detector. The determination of operation 1320 can be made also from a motion detector signal generated by the motion detector.

If at operation 1320 the answer is yes, then according to another operation 1350, a transmitted sound can be output, for example via a speaker system. The transmitted sound can communicate a request to check a pulse of the patient, and/or include the words: "Pulseless Electrical Activity" or the initials: "P.E.A.". In addition, the transmitted sound can be and/or communicate other items, as described above.

In some embodiments, if at operation 1320 the answer is yes, then according to another, optional operation 1330, an alerting mechanism is activated. According to another, optional operation 1340, it is determined whether an entry is received in an inputting mechanism. The entry would be received, for example, within a certain time period, responsive to the alerting mechanism being activated, and its receipt could be used as an additional criterion of P.E.A. It, at operation 1340 no entry is received, then execution may continue to operation 1350. Else, it may exit flowchart 1300.

Figure 14:
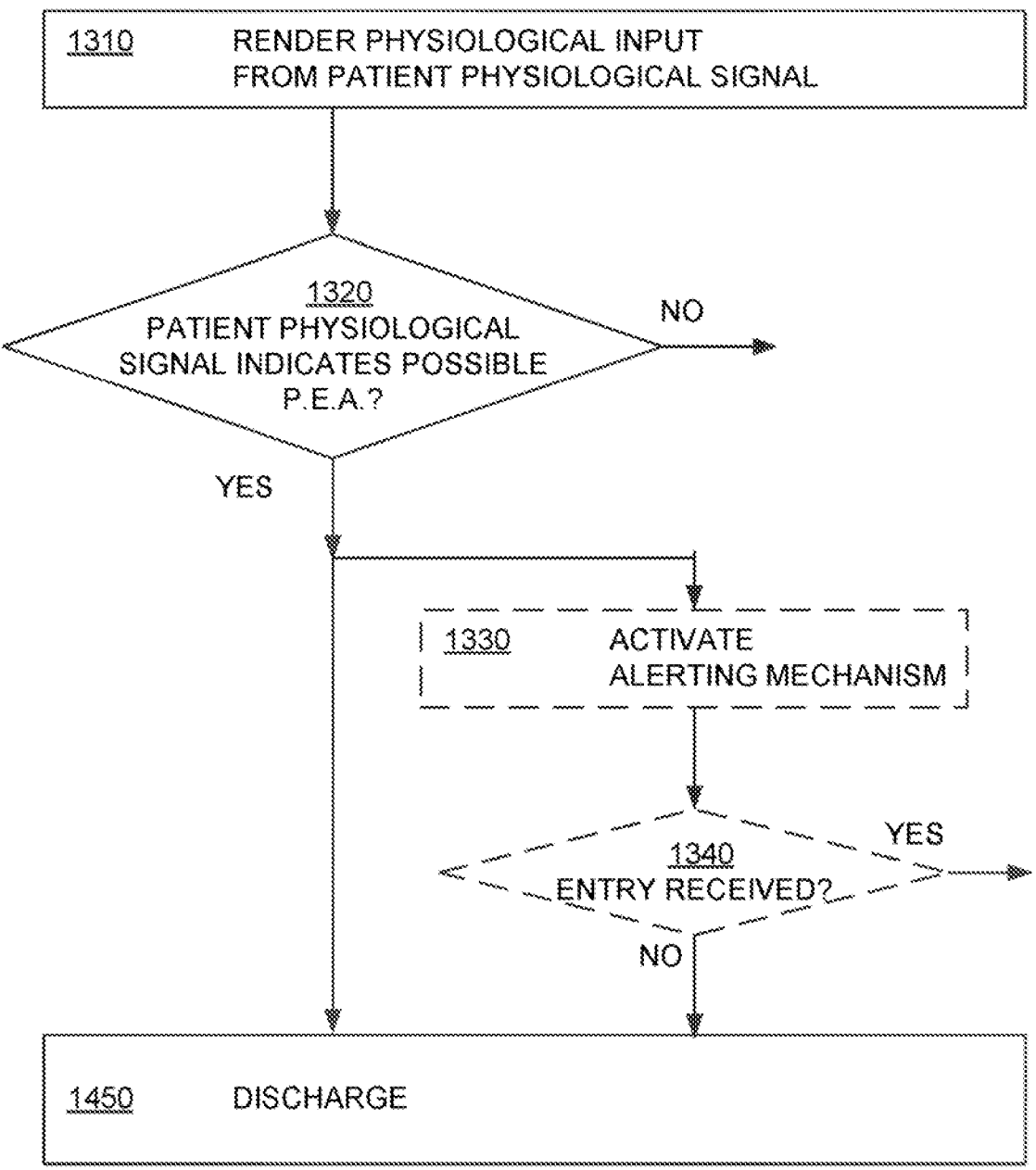
FIG. 14 is a flowchart for illustrating sample P.E.A. methods according to embodiments.

FIG. 14 shows a flowchart 1400 for describing methods according to embodiments. The methods of flowchart 1400 may also be practiced by WCD system 1202 and other embodiments described in this document.

Flowchart 1400 includes operations 1310, 1320, 1330, 1340 that were described previously, with reference to FIG. 13. However, instead of operation 1350, according to another operation 1450, a discharge circuit can be controlled to discharge electrical charge through the patient. Previously mentioned additional features and extensions may be implemented also in the methods of flowchart 1400.

In embodiments, a WCD system may request a bystander to place a mobile communication device close, i.e. to the speaker system, to the WCD system, etc. The speaker system may transmit sounds that communicate aspects of the patient and the event, and which may be thus received by a remote facility, such as a care center. Examples are now described.

Figure 15:
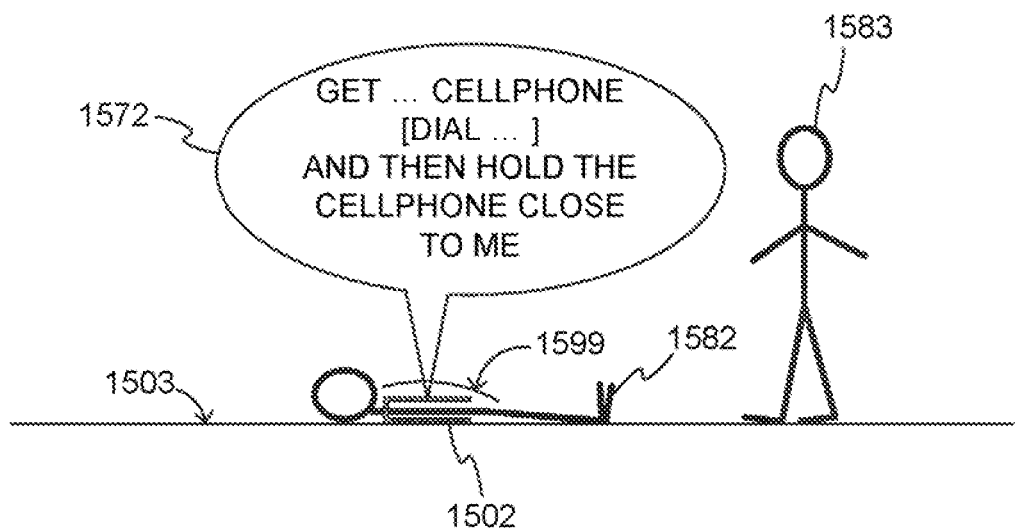
FIGS. 15 and 16 are diagrams of sample successive scenes for illustrating how a bystander may help with a mobile communication device according to embodiments.
Figure 16:
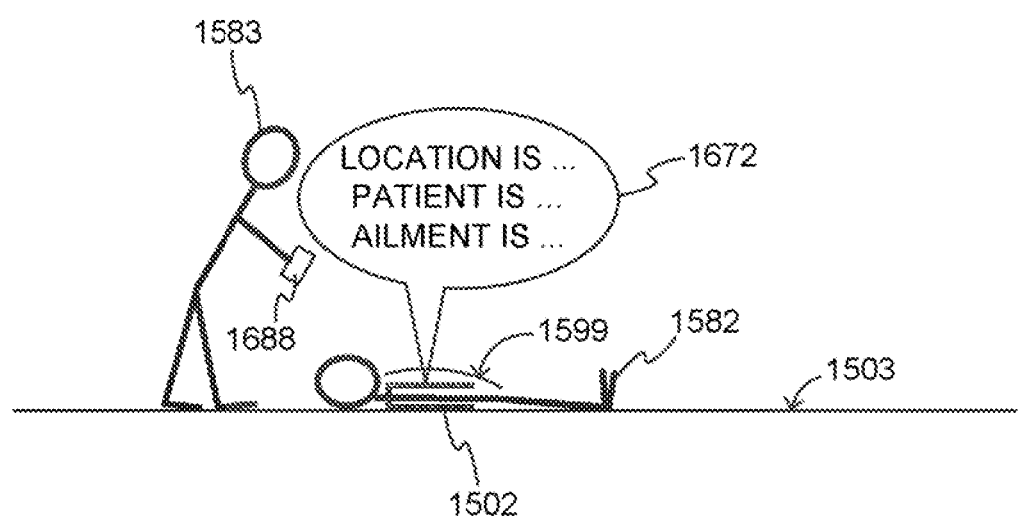

FIGS. 15 and 16 are diagrams of successive scenes for illustrating how a bystander may help with a mobile communication device according to embodiments. In FIG. 15 a patient 1582 has fallen on ground 1503, in an emergency. Patient 1582 is wearing a WCD system 1502, and an outer garment 1599. A bystander 1583 might be nearby.

From collection 302 of FIG. 3, WCD system 1502 may include support structure 370, energy storage module 350, discharge circuit 355, and speaker system 374. Speaker system 374 can be configured to output a transmitted sound 1572. Transmitted sound 1572 may communicate a request to bystander 1583 to place a mobile communication device proximately to the speaker system.

While sample words are shown in FIG. 15, the request may be implemented in any number of ways. For example, the requested mobile communication device may be that of patient 1582, which is to be removed from their body, or that of bystander 1583. For another example, the device requested for might not be called "mobile communication device", but instead transmitted sound 1572 might include enunciated words such as "PHONE", "CELLPHONE", "TELEPHONE", "SMARTPHONE", or "MOBILE PHONE".

Additionally, the request might not be explicitly for placing the device proximately to the speaker system, but it could be phrased in other ways. For example, it could call for placing it close to something that is proximate to the speaker system, such as "the patient", and so on. It might even call for placing the device onto the patient, or maintain it close to the patient but without it touching the patient at all.

In some embodiments, transmitted sound 1572 further requests bystander 1583 to dial a specific telephone number on the mobile communication device, prior to so placing it. This number can be "911" in the US, or a number specifically designed for this type of occurrence.

The scene of FIG. 16 may occur shortly after the scene of FIG. 15. In FIG. 16 bystander 1583 has placed a mobile communication device 1688 near patient 1582. The speaker system of WCD system 1502 now outputs transmitted sound 1672, which may be heard by cellphone 1688. This permits WCD system 1502 to communicate via the cellphone with a remote care giver that has been dialed, and transmit information. Alternately, the dialed facility can be a server that merely records the transmitted sound 1672. If it is known that the dialed facility is indeed a server, the transmission can be made by machine sounds, such as DTMF, which need not be understandable by humans.

WCD system 1502 can transmit many types of information this way. In some embodiments, WCD system 1502 also includes memory 338, which has been configured to store one or more data files. The one or more data files may encode patient data about the patient or a medical provider related to the patient or WCD system itself. Transmitted sound 1672 can further communicate the patient data.

In some embodiments, WCD system 1502 also includes measurement circuit 320, which has been configured to render a physiological input from a patient physiological signal. Transmitted sound 1672 can further communicate the physiological input. In some of these embodiments, WCD system 1502 further includes a processor configured to determine from the physiological input an ailment of the patient. Transmitted sound 1672 can further communicate the determined ailment.

In some embodiments, WCD system 1502 additionally includes location sensor 386. Transmitted sound 1672 can further communicate the detected location.

During these transmissions, the attention of bystander 1583 may drift. Transmitted sound 1672 can further communicate a reminder to place or maintain the mobile communication device 1688 proximately to the speaker system.

WCD system 1502 may establish more of a handshake with mobile communication device 1688. For example, bystander 1583 may be asked to press a button on device 1688 upon initially receiving a response, and before placing the device as requested. Plus, instructions in human language may be received from device 1688.

In some embodiments, WCD system 1502 may receive instructions and data directly from device 1688, and in particular from the party that has been accessed, for example in machine voice. For a particular example, WCD system 1502 may further include microphone 376 that is configured to sense an ambient sound, and state machine 331. State machine 331 can be configured to be in a first internal state, a second internal state, and so on, depending on what it is intended to do, such as deliver therapy, report, standby, self-diagnose, and so on. In such embodiments, the sensed ambient sound may emanate from mobile communication device 1688, and encode a command. State machine 331 may revert from the first internal state to the second internal state, responsive to the command.

Figure 17:
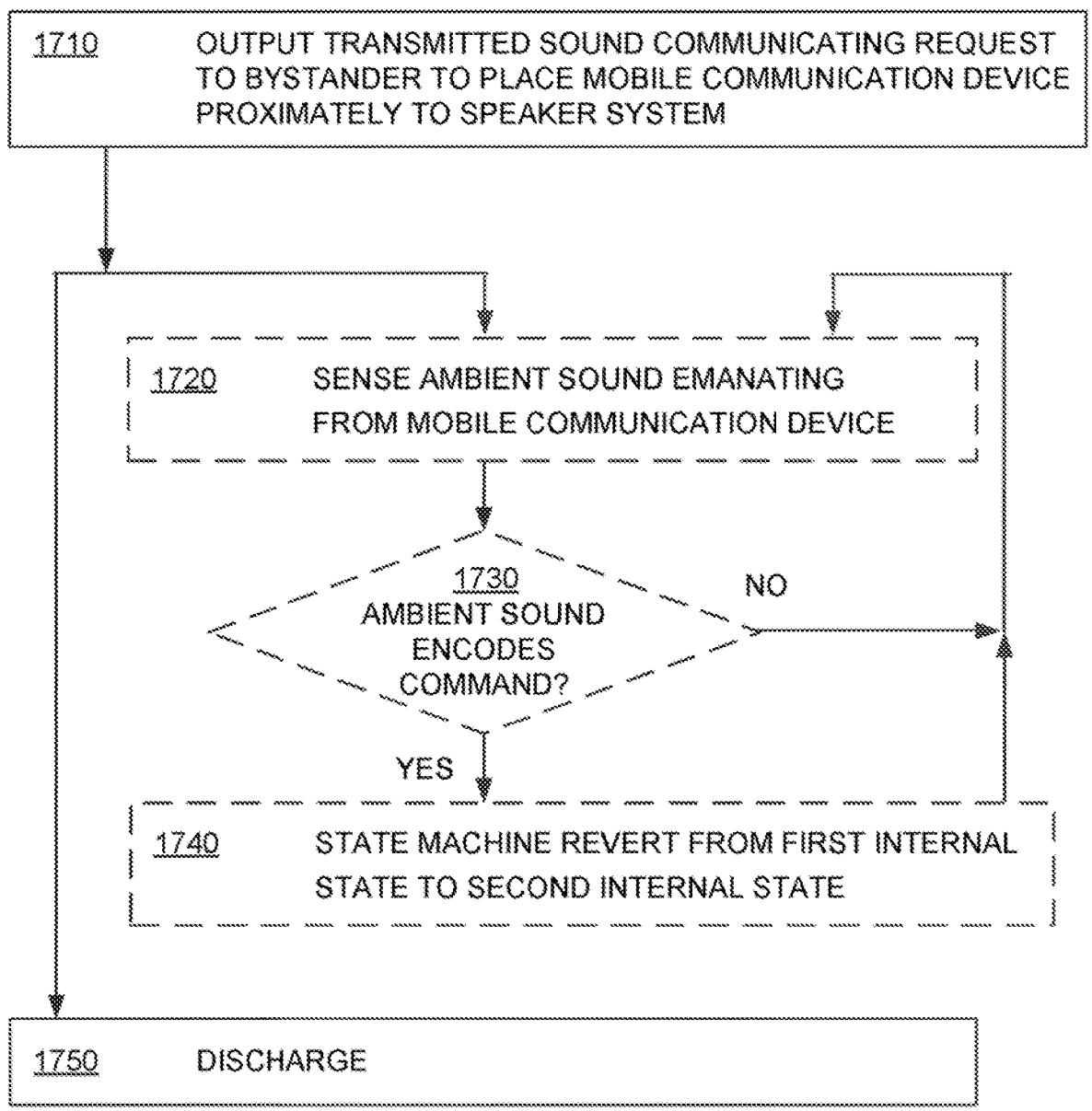
FIG. 17 is a flowchart for illustrating sample methods according to embodiments.

FIG. 17 shows a flowchart 1700 for describing methods according to embodiments. The methods of flowchart 1700 may also be practiced by WCD system 1502 and other embodiments described in this document.

According to an operation 1710, a transmitted sound is output, for example by the speaker system, while the support structure is worn by the patient. The transmitted sound may communicate a request to a bystander to place a mobile communication device proximately to the speaker system. Other examples were seen above.

According to a subsequent operation 1750, the discharge circuit can be controlled to discharge an electrical charge through the patient. Alternately, a number of optional operations may be executed, alone or in conjunction with operation 1750.

In particular, according to another, optional operation 1720, an ambient sound may be sensed, which emanates from the mobile communication device. According to another, optional operation 1730, it can be inquired whether or not the sensed ambient sound encodes a command, which is likely intended for WCD system 1502. If not, execution may revert to operation 1720. If yes, then according to another, optional operation 1740, a state machine may revert from a first internal state to a second internal state, responsive to the command.

Embodiments face uncertainties about bystanders, starting from whether anyone is there or not. Even if someone is there, that someone is not necessarily a person committed to helping, as is the case for someone who rushes over to an emergency scene with an AED Rather, a bystander in a WCD context does not necessarily know initially that a WMS system is already applied to the patient. This person could range anywhere from a person who is initially indifferent, to a person who may pay attention, to a person who may become engaged (possibly unhelpfully), to a person who may be willing to do CPR (possibly inadequately), to a person who may do some CPR adequately but then stop, to a trained first responder, to a responder who is trained for a patient wearing a WCD system.

A certain set of WCD system embodiments prepare for one or more of these eventualities. Some embodiments may focus on whether or not a bystander is willing to perform CPR and able to perform adequate CPR, and implement dual mode operation, with switching between the modes. If implemented, state machine 331 may indicate the current mode. An example of these modes, and switching between them, is now described.

Figure 18:
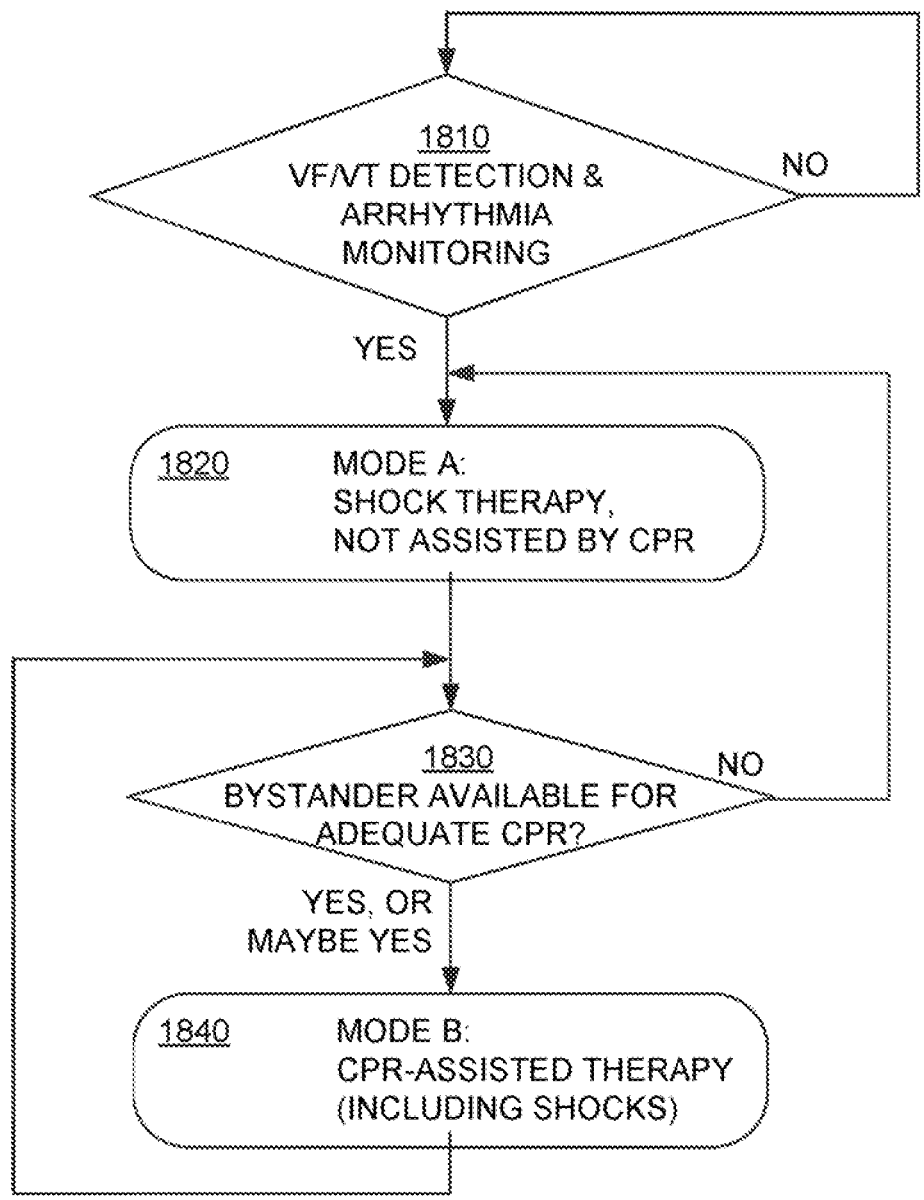
FIG. 18 is a flowchart for illustrating a sample dual mode operation according to embodiments.

FIG. 18 shows a flowchart 1800 for describing dual mode methods according to embodiments. The methods of flowchart 1800 may also be practiced by WCD system embodiments described in this document. It will be appreciated that many other features described in this document can be part of the dual mode methods of flowchart 1800.

According to an operation 1810, a WCD system detects for Ventricular Fibrillation (VF) or Ventricular Tachycardia (VT), or monitors for other heart arrhythmias. For as long as no such problem is detected, execution can loop back to operation 1810. In addition, as part of operation 1810, a WCD system may monitor for bystanders who are close, preferably passively. Such passive monitoring may be as described in this document, for example by their voices, sounds, capacitance meter, and so on. Upon so monitoring, a system may set corresponding internal flags accordingly, in case a need arises.

If at operation 1810 VF or VT are detected, then operations of a possible Mode A 1820 may be performed. These operations include administering electrical shock therapy, which may be one shock, or a stack of two or more shocks. These operations further may include re-detection of VF/VT, checking a therapy protocol for completion, and so on. Mode A 1820 may be exited upon a therapy protocol being completed.

According to a subsequent operation 1830, it is determined whether a bystander is available for performing adequate CPR. This can be a multi-step operation, since it may not be initially known whether or not a) a bystander is there, b) is willing to perform CPR, and c) the CPR will be adequate. Elements of operation 1830 may include that prompts may be issued to bystanders, bystanders may be sensed, and their CPR may be sensed, using at least examples given in this document. It will also be appreciated that some of these elements of operation 1830 may be performed also while looping through operation 1810, and also within the operations of Mode A 1820. If at operation 1830 the answer is no, then execution may revert to Mode A 1820, given that there is no other option, or may have other protocols.

If at operation 1830 the answer is yes or maybe yes, then the operations of a Mode B 1840 may be opportunistically performed. Of course, answering the question of operation 1830 as "yes" or "no" can be implemented by deriving a confidence score, and determining whether the confidence score is higher than a decision threshold. Here the decision threshold can be set to favor also the answer "maybe yes", so as to favor the opportunistic use of Mode B 1840. For example, an announcement can be made requesting engagement, and a timer can be started. If the timer reaches a limit without a qualifying event happening, then the answer can become "no", and execution may revert to Mode A 1820. A qualifying event can be that a person's voice was heard, with some confidence that it was in response to a prompt, or a proximity detector triggered, or touching was detected. Of course, if a bystander engages only to speak and interact but not to do CPR for some prolonged time interval, the answer can be again deemed to be no.

Within Mode B 1840, therapy may proceed in a different mode, where therapy is assisted by CPR. Sequences of CPR compressions may be expected from the bystander, who has now become a rescuer. As will be seen below, a WCD system may further have a speaker system that emits CPR prompts so as to assist these sequences of compressions. Then the rescuer may be asked to no longer touch the patient, shock, then re-detect for VF/VT, ask for more CPR, and so on. In addition, embodiments may exit Mode B 1840 at various operations or points in time, which returns execution to operation 1830, to ensure the continuing availability of a bystander available to perform adequate CPR.

In such operations alerts may be set accordingly, and therapy may be enabled or disabled accordingly. Moreover, while the operations of flowchart 1800 are focused on CPR, additional prompts may ask other bystanders for help, ask them to dial 911 and report on their own, and so on.

In embodiments, a WCD system may emit CPR prompts. A speaker system can transmit a sound that has periodic contents designed to assist a bystander to perform CPR. Such may help after a defibrillation shock, and also in the event of P.E.A. and maybe asystole, and so on. Optionally CPR chest compressions are detected, and feedback can be given. An example is now described.

Figure 19:
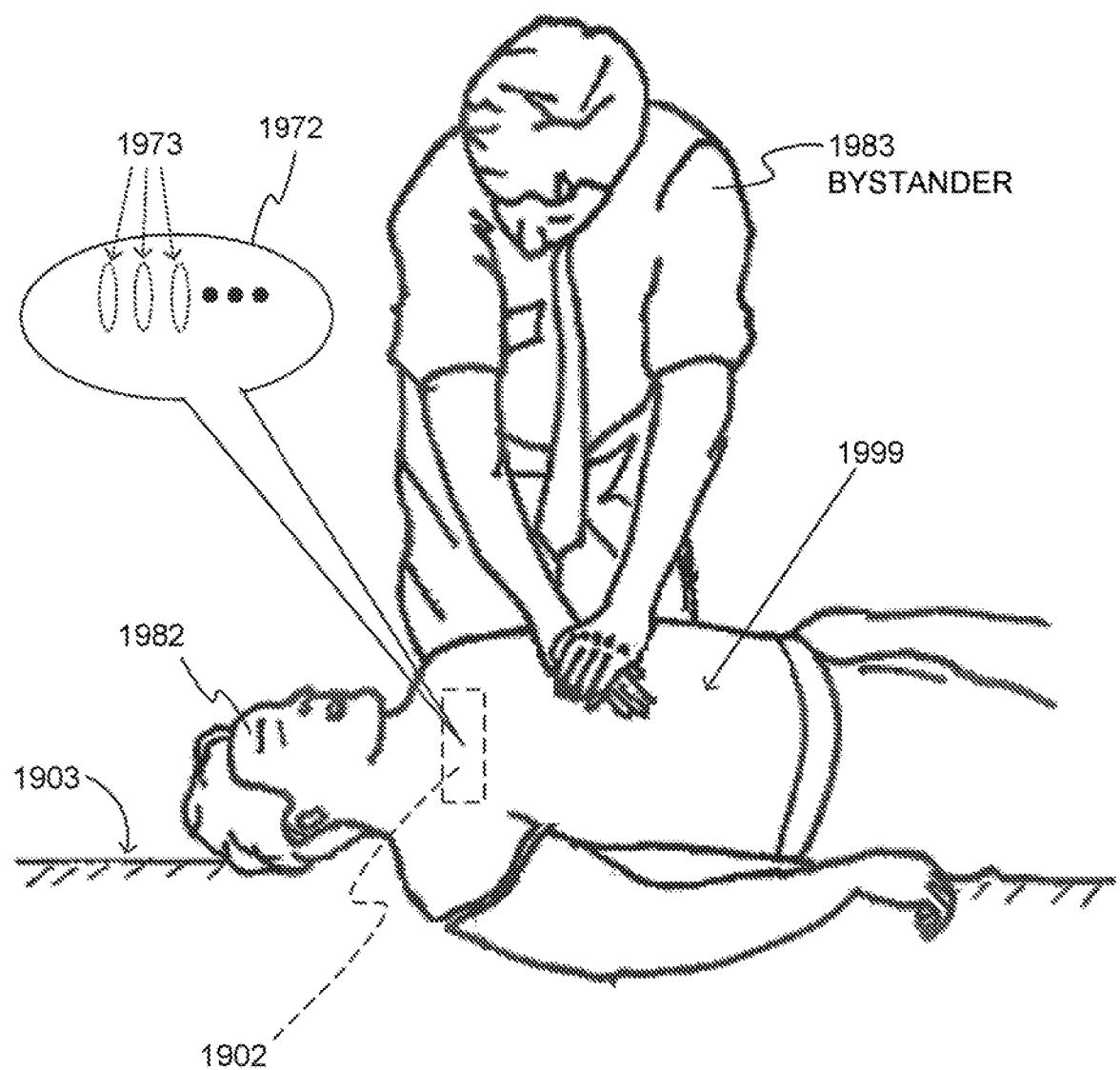
FIG. 19 is a diagram of a scene where a sample WCD system transmits sounds that are designed to assist a bystander to perform CPR according to embodiments.

FIG. 19 is a diagram of a sample scene, where a patient 1982 has fallen on ground 1903, in an emergency. Patient 1982 is wearing an outer garment 1999. Patient 1982 is also wearing a WCD system 1902, of which only a small portion is shown, and in dashed lines, as it is obscured by outer garment 1999. A bystander 1983 has been engaged, and is performing CPR chest compressions on patient 1982.

From collection 302 of FIG. 3, WCD system 1902 may include processor 330, support structure 370, energy storage module 350, and discharge circuit 355. It may also have speaker system 374, which has been configured to output a transmitted sound 1972. In this example, transmitted sound 1972 has substantially periodic contents 1973. Contents 1973 may be designed to assist bystander 1983 to perform CPR chest compressions to patient 1982. For example, contents 1973 may be sequences of tones, to which bystander 1983 can synchronize their sequences of compressions—in other words a metronome-type sound. Transmitted sound 1972 may further communicate a request to not remove the support structure from the patient. In addition, transmitted sound 1972 can further communicate reminders to perform CPR ventilations as part of the overall CPR. Related transmitted sounds, or images, can assure bystander 1983 that no shock is impending, that there will be ample notification well before a shock is prepared, and that shock will not happen before bystander 1983 is ready.

In a number of embodiments of WCD system 1902, CPR chest compressions that are performed on patient 1982 are detected. Detection may be in a number of ways. In some embodiments, WCD system 1902 includes one or more motion detectors 384, which can be coupled to the support structure. This way, the performed CPR chest compressions can be detected by the one or more motion detectors 384. Moreover, at least one of motion detectors 384 can be coupled to the support structure at such a point as to be near the sternum of patient 1982, and at least one of motion detectors 384 can be coupled to the support structure at such a point as to be near the back of patient 1982. Alternately or in addition, WCD system 1902 can have an impedance sensing module, for example from measurement circuit 320; in such cases, the performed CPR chest compressions can be detected by the impedance sensing module, as the CPR chest compressions affect the patient impedance.

In embodiments of WCD system 1902 where performed CPR chest compressions are detected, feedback may be additionally communicated to the user. The feedback may refer at least to a depth or to a rate of the detected CPR chest compressions. The feedback can be communicated in a number of ways. For example, in some embodiments the feedback is communicated by transmitted sound 1972. In other embodiments, the feedback is communicated by visual representations on screen 375 on WCD system 1902. Suitable sounds and representations may be learned from the art of CPR feedback devices.

In some embodiments, the detected CPR chest compressions are recorded, along with other events. The detected CPR chest compressions may be analyzed, Figures of Merit may be computed, and so on. It should be remembered that, unless more is known, bystander 1983 is likely not a trained first responder, but a well-meaning Good Samaritan who may have even learned First Aid and CPR, but many years prior and may have forgotten some of it.

In some embodiments, WCD system 1902 makes further provisions for shocking the patient after CPR is received. Accordingly, transmitted sound 1972 may further communicate a request for bystander 1983 to no longer touch patient 1982. This request may be communicated after at least two minutes of detecting chest compressions, in which case it may be judged that patient 1982 has received some benefit from the CPR. In some embodiments, the request to no longer touch the patient can be communicated less than two minutes after detecting the chest compressions, for example in cases where it is judged that the CPR is poor, and not improving despite any prompts or feedback.

The request to not touch the patient may be communicated anyway as a safety feature, even if bystander 1983 has not yet touched patient 1982. It could be that no bystander gave CPR, but someone was preparing to do so.

In some embodiments, additional provisions for shocking the patient after CPR can include that transmitted sound 1972 further communicates a request to say one or more preset affirmative words, such as "CLEAR", "YES", or "ALL CLEAR". It may be possible to be able to detect reliably every time whether bystander 1983 is no longer touching patient 1982, but engaging bystander 1983 this way may also help. In some of these embodiments, WCD system 1902 further includes microphone 376 coupled to the support structure. Microphone 376 can be configured to sense an ambient sound, and the electrical charge can be discharged through the patient responsive to the sensed ambient sound including one or more of the preset affirmative words.

Figure 20:
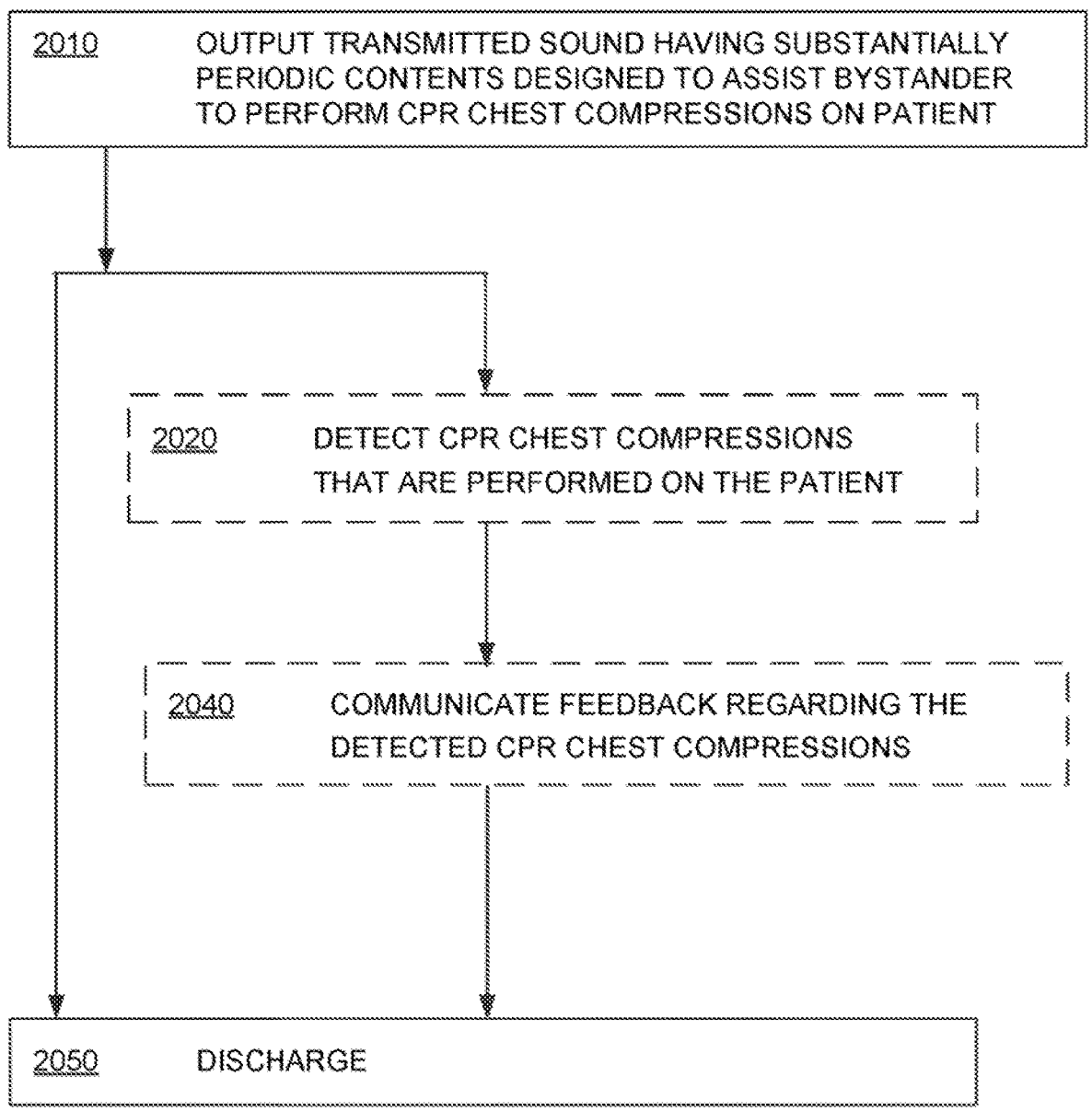
FIG. 20 is a flowchart for illustrating sample methods according to embodiments.

FIG. 20 shows a flowchart 2000 for describing methods according to embodiments that are related to the above description. The methods of flowchart 2000 may also be practiced by WCD system 1902 and other embodiments described in this document.

According to an operation 2010, a transmitted sound is output. The transmitted sound may have substantially periodic contents, which may be designed to assist a bystander to perform CPR chest compressions on a patient. This may be performed while a support structure is worn by the patient.

According to a subsequent, optional operation 2020, CPR chest compressions that are performed on the patient may be detected. This may be performed in a number of ways, including as described above.

According to another optional operation 2040, feedback is communicated regarding the CPR chest compressions detected in operation 2020. The feedback can be communicated in a number of ways, for example as described above.

According to another operation 2050, a discharge circuit is controlled to discharge electrical charge through the patient. Again, this may be performed while the support structure is worn by the patient.

In addition, what was written above for WCD system 1902 may augment the methods of flowchart 2000.

In embodiments, a WCD system may emit different CPR prompts for different bystanders. The WCD system may include a user interface that can differentiate among bystanders. The user interface may output CPR prompts that are tailored to a skill level of the bystander. An example is now described.

In some embodiments, a WCD system (not shown separately) may include support structure 370, energy storage module 350, discharge circuit 355, and user interface 373 from collection 302 of FIG. 3. User interface 373 can be configured to receive a usage input from a bystander, for example as described above. The usage input may relate to a skill of the bystander, as self-reported by the bystander, or looked up, or even authenticated.

User interface 373 may include a speaker system 374 that is configured to output a transmitted sound having substantially periodic contents, which are designed to assist a bystander to perform CPR chest compressions on the patient, for example as described above for contents 1973. The transmitted sound may also include a request for the usage input.

In embodiments, an aspect of the contents can be different responsive to a received usage input. A variety of implementations are possible. For example, the aspect can be different if a usage input is received than if not received, and so on. The aspect can be a frequency of the contents, a number of tones within a sequence for the compressions, a number of sequences of compressions between shocks, a total number of tones before the next discharge that could reflect a duration of a CPR period, whether or not to perform ventilations, etc. For example, if a usage input by the bystander reports that the by stander is too tired to do any more CPR, no more CPR might be asked of them, and so on.

Figure 21:
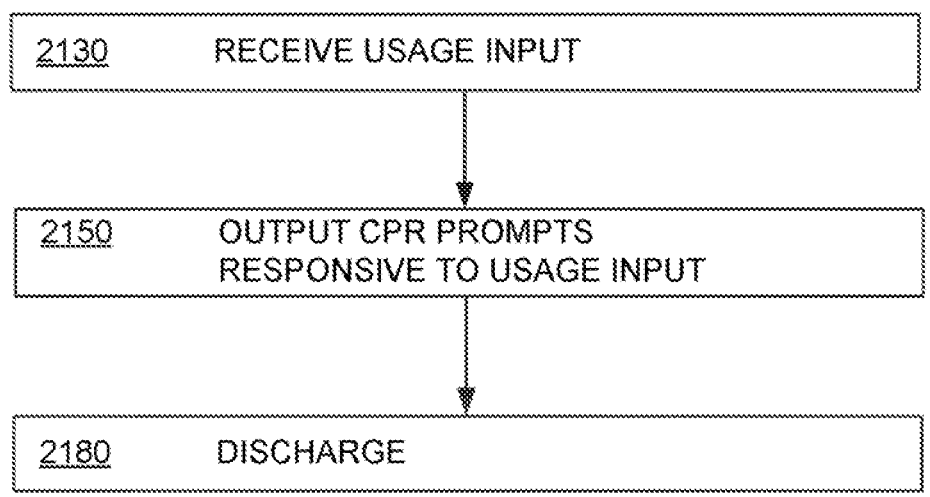
FIG. 21 is a flowchart for illustrating sample methods according to embodiments.

FIG. 21 shows a flowchart 2100 for describing methods according to embodiments. The methods of flowchart 2100 may also be practiced by embodiments described in this document.

According to an operation 2130, a usage input may be received. The usage input may be received in the user interface, and be of the type that a bystander enters to control a WCD system, whether unassisted or by listening over the telephone to a remote care center.

According to another operation 2150, a transmitted sound can be output, for example via a speaker system. The transmitted sound can have substantially periodic contents, which are designed to assist a bystander to perform CPR chest compressions on the patient. Accordingly, they can be CPR prompts, for example as described above. An aspect of these contents can be different responsive to the received usage input, as described above.

According to another operation 2180, the discharge circuit can be controlled to discharge the electrical charge through the patient, while the support structure is worn by the patient.

In embodiments, a WCD system might be ready to deliver a shock, but may not deliver it, if it hears a bystander say a preset delaying word such as "NO". An example is now described.

Figure 22:
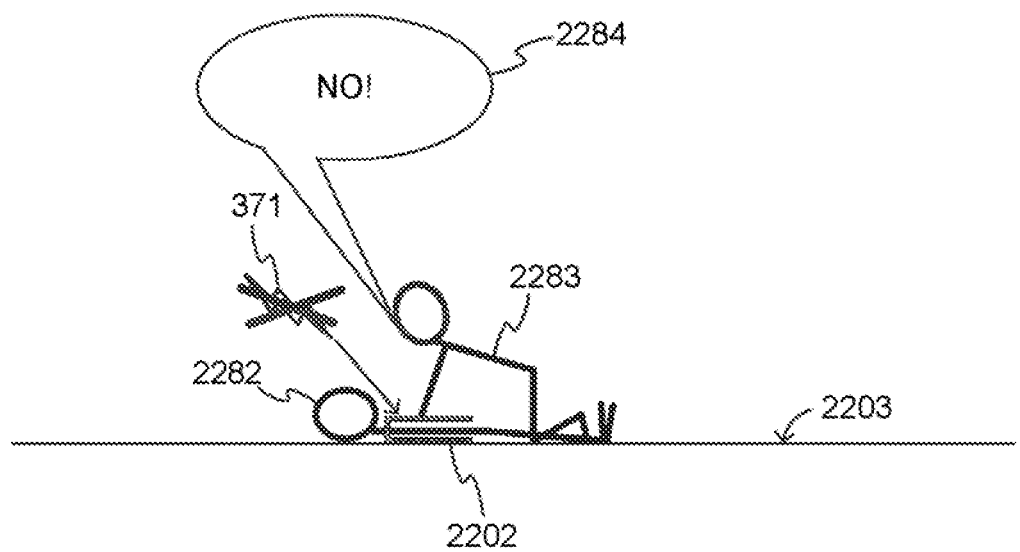
FIG. 22 is a diagram of a scene where a sample WCD system according to embodiments is prevented from shocking a patient if it hears a delaying word such as "NO".

FIG. 22 is a diagram of a sample scene, where a patient 2282 has fallen on ground 2203, in an emergency. Patient 2282 is wearing a WCD system 2202, but no outer garment.

A bystander 2283 has been engaged, and is performing CPR chest compressions on patient 2282, over WCD system 2202.

WCD system 2202 can be better prepared for this eventuality. For example, support structure 370 of WCD system 2202 may include an indicator pointing at a place on the sternum of patient 2282, where the palms of bystander 2283 should be placed.

In FIG. 22, bystander 2283 is saying "NO". (For purposes of this document, a bystander saying something also includes the bystander shouting it.) When bystander 2283 speaks, he is creating an ambient sound 2284. In the example of FIG. 22, ambient sound 2284 includes the word "NO".

From collection 302 of FIG. 3, WCD system 2202 may include processor 330, support structure 370, energy storage module 350, discharge circuit 355, and microphone 376. In some embodiments, WCD system 2202 additionally includes a head set configured to be worn by a rescuer. In such embodiments, microphone 376 may be coupled to the head set. In addition, processor 330 can be further configured to prevent the electrical charge from being discharged through the patient, responsive to the sensed ambient sound including a preset delaying word. In this example, such a preset delaying word is "NO", but other words can be used such as "WAIT", etc. Since "NO" is said, discharge 371 does not happen in the example of FIG. 22.

The bystander's saying "NO" could take place in a number of ways, for example it can be elicited by WCD system 2202. More particularly, and as will be seen later in this document, WCD system 2202 may have a speaker system or a display through which it posed suitable a question, to which bystander 2283 is replying. Here the question can be "PREPARING TO SHOCK THE PATIENT—HAVE YOU LET GO YET?" By replying "NO", bystander 2283 gains more time to release patient 2282, so that he will not be shocked along with patient 2282.

Processor 330 may include enough voice recognition capability for recognizing preset delaying words and preset ready words from ambient sounds. WCD system 2202 may further include memory 338, which has been configured to store one or more data files that encode one or more of the preset delaying words. In addition, dialogue scenarios may be planned so that possible preset responses differ, for easier recognition. And it should be remembered that the voice of bystander 2283 may be impacted by the circumstances. Indeed, bystander 2283 may be justifiably out of breath, stressed upon thinking that patient 2282 may die, and possibly even frantic if patient 2282 is a loved one. Accordingly, short and clear preset words may work well, in planning the dialogue.

In a related method that may be practiced by WCD system 2202 and/or its processor, an ambient sound may be sensed by the microphone. The ambient sound may be sensed while the support structure is worn by the patient. Then the discharge circuit can be controlled so as to prevent the electrical charge from being discharged through the patient, responsive to the sensed ambient sound including a preset delaying word.

In embodiments, a WCD system may be ready to deliver a shock, but may first wait before doing so until it hears from a bystander a preset ready word, such as: "CLEAR". An example is now described.

Figure 23:
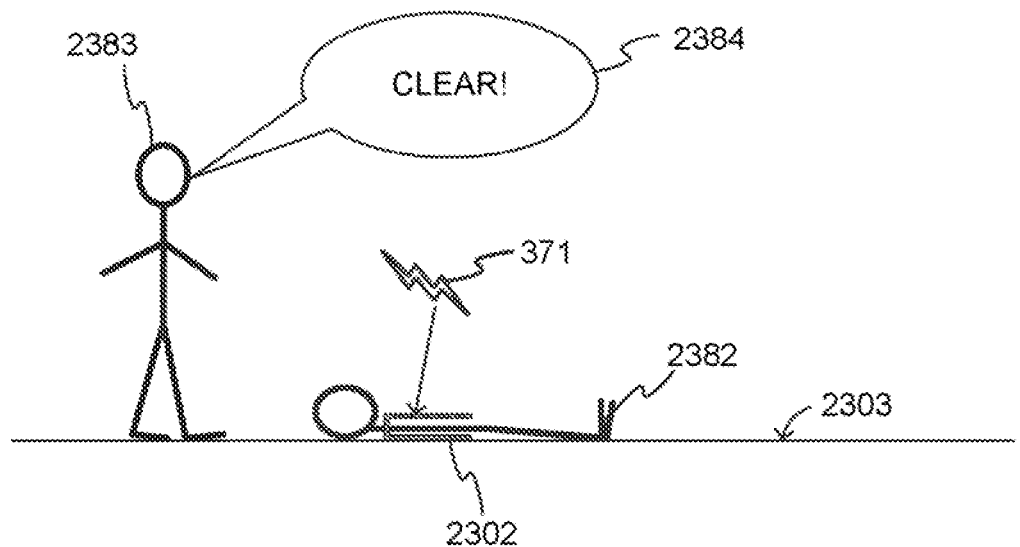
FIG. 23 is a diagram of a scene where a sample WCD system according to embodiments shocks a patient only after hearing a preset ready word, such as "CLEAR".

FIG. 23 is a diagram of a sample scene, where a patient 2382 has fallen on ground 2303, in an emergency. Patient 2382 is wearing a WCD system 2302, but no outer garment. A bystander 2383 has been engaged, and is not touching patient 2382. Perhaps bystander 2383 has performed CPR on patient 2382; while now he is no longer touching patient 2382, he is still engaged in the event.

In FIG. 23, bystander 2383 is saying "CLEAR". When bystander 2383 speaks, he is creating an ambient sound 2384. In the example of FIG. 23, ambient sound 2384 includes the word "CLEAR".

From collection 302 of FIG. 3, WCD system 2302 may include processor 330, support structure 370, energy storage module 350, discharge circuit 355, and microphone 376. In some embodiments, WCD system 2302 additionally includes a head set configured to be worn by a rescuer, who could be the bystander. In such embodiments, microphone 376 may be coupled to the head set. In addition, processor 330 may be further configured to prevent the discharge circuit from discharging the electrical charge through the patient, but permit it to be so discharged responsive to the sensed ambient sound including one or more preset ready words. In this example, such a preset ready word is "CLEAR", but other words can be used such as "YES", "ALL CLEAR" etc. Since "CLEAR" is said, discharge 371 takes place in the example of FIG. 23.

Again, the word "CLEAR" can be elicited by WCD system 2302. WCD system 2302 may have a speaker system or a display through which it posed a question, to which bystander 2383 is replying. By replying "CLEAR", bystander 2383 confirms for WCD system 2302 that it is safe to shock patient 2382.

As with the previous embodiment, processor 330 may include enough voice recognition capability, and WCD system 2302 may further include memory 338, which has been configured to store one or more data files that encode one or more of the preset ready words. And it should be remembered that bystander 2383 may be farther from the microphone when saying "CLEAR", than in the previous embodiment.

It will be recognized that a single embodiment of a WCD system could have the features described in conjunction with both FIG. 22 and FIG. 23. In such a case, the scene of FIG. 23 could simply happen after the scene of FIG. 22, for example after enough CPR.

In a related method that may be practiced by WCD system 2302 and/or its processor, a discharge circuit may be prevented from discharging an electrical charge through the patient. Then an ambient sound may be sensed by the microphone. The ambient sound may be sensed while the support structure is worn by the patient. Then the discharge circuit can permit to discharge the electrical charge through the patient responsive to the sensed ambient sound including one or more preset ready words.

In embodiments, a WCD system may transmit a sound requesting a bystander to speak. A bystander's answer may be recorded. The sensed speech may be even interpreted for operation. An example is now described.

FIG. 24 is a diagram of a sample scene, where a patient 2482 has fallen on ground 2403, in an emergency. Patient 2482 is wearing a WCD system 2402, but no outer garment. A bystander 2483 has been engaged, and is performing CPR chest compressions on patient 2482, over WCD system 2402.

From collection 302 of FIG. 3, WCD system 2402 may include processor 330, support structure 370, energy storage module 350, discharge circuit 355, speaker system 374, possibly screen 375, microphone 376 and memory 338. In some embodiments, WCD system 2402 additionally includes a head set configured to be worn by a rescuer. In such embodiments, microphone 376 may be coupled to the head set.

In FIG. 24, speaker system 374 outputs a transmitted sound 2472. Transmitted sound 2472 may communicate a request to bystander 2483 to speak. If bystander 2483 does speak, an ambient sound will be created, of which examples were seen in FIGS. 22 and 23. Microphone 376 may sense the created ambient sound created by bystander 2483. In addition, memory 338 may store one or more data files that contain a recording made from the sensed ambient sound. The one or more data files can become a record of the event, or be discarded. For example, transmitted sound 2472 may ask about the surrounding circumstances, and so on.

The electrical charge can be discharged, in the form of a shock, before the transmitted sound is output, and/or afterwards. In some embodiments, the transmitted sound, before communicating the request to bystander 2483 to speak, was used to assist CPR. Accordingly, before so requesting, the transmitted sound had substantially periodic contents designed to assist bystander 2483 to perform CPR chest compressions on patient 2482, along with possibly other content.

In some embodiments, the reply of bystander 2483 is intended to be recognized without much delay. Processor 330 may include enough voice recognition capability for this effect.

In some particular embodiments, the transmitted sound communicates a request to say one or more preset words, so that the ambient sound is more readily recognizable. In FIG. 24, the preset word is "CLEAR", but of course other words are possible. Specific words chosen in advance can be called preset words. Above examples are described of two sample classes of such preset words, namely preset delaying words and preset ready words. Other sample preset words include "YES", "ALL CLEAR", "NO" and "WAIT". In addition, the request can be displayed on screen 375, or the request can operate in combination with what is displayed on screen 375. Again, the words may be chosen in terms of context.

If the bystander indeed says one of the preset words, they may further help the operation of WCD system 2402 as these words are recognized. For example, the electrical charge can be prevented from being discharged through the patient, responsive to the sensed ambient sound including a preset word, as seen previously for "NO" and "WAIT". For another example, the discharge circuit can be prevented from discharging the electrical charge through the patient, but permitted to so discharge responsive to the sensed ambient sound including a preset word. As seen previously, such preset words can be "CLEAR", "YES", and "ALL CLEAR".

FIG. 25 shows a flowchart 2500 for describing methods according to embodiments. The methods of flowchart 2500 may also be practiced by WCD system 2402 and other embodiments described in this document.

According to an operation 2510, a transmitted sound may be output, for example via a speaker system. The transmitted sound may communicate a request to a bystander to speak. If the bystander does speak, an ambient sound will be created.

According to another operation 2520, the created ambient sound may be sensed, for example via a microphone. According to another operation 2540, one or more data files can be stored in a memory. The one or more data files may contain a recording made from the sensed ambient sound.

According to another operation 2550, discharge may take place, while the support structure is worn by the patient. In particular, a discharge circuit may be controlled to discharge an electrical charge through the patient. Variations and enrichments described with reference to FIG. 24 may also be applied to the methods of flowchart 2500.

In additional embodiments, provisions can be made for the engagement of a bystander not proceeding optimally. For example, a WCD system may have different modes that it can switch to, depending on what it infers the bystander is doing. In some embodiments, if the bystander's answer is not understood, a prompt may be repeated. Sensed ambient sounds may be examined as to whether they are intended to be answers in the first place, depending on their consistency and timeliness after a prompt is issued. It is possible that a bystander will abandon the effort, in which case the WCD system may want to continue without help, and so on.

In further embodiments, provisions can be made for the event that the cancel switch is actuated inappropriately, for instance if the patient has fallen on their chest in a way that presses a cancel switch button by the patient's own weight. For one example, it may be inferred that if the cancel switch is being actuated without a warning having been issued about it, that such an actuation is not legitimate. In such cases, the risk is that a potentially life-saving electric shock might not be administered. Examples are now described.

In embodiments, a WCD system may include a cancel switch whose actuation can cancel an impending shock, but it may ignore the actuation if it is inappropriate. Motion data from a motion detector may help determine if the actuation is inappropriate.

In some embodiments, a WCD system may include support structure 370, energy storage module 350, measurement circuit 320, processor 330, discharge circuit 355, cancel switch 377 and motion detector 384, from collection 302 of FIG. 3.

Motion data that is generated by motion detector 384 may be analyzed, for example by processor 330. The analysis can be as to whether the motion data supports the inference that the patient, who is wearing the support structure, is actually the one actuating cancel switch 377. For example, if the patient has stopped moving for a while, possibly consistently with a life-threatening cardiac event, and then cancel switch 377 is actuated while the patient continues to be motionless, the actuation may be deemed spurious. Indeed, the actuation may be from how components may contact each other, or their immediate physical environment. The patient may have fallen forward on his chest. In particular embodiments, if it is determined that the motion data meets a spuriousness threshold, then the actuation of the cancel switch may be ignored, and discharging is thus not prevented.

An actuation that is deemed spurious may be even done by a bystander, who is well-meaning but does not know better. Indeed, the bystander might hear a warning about the impending shock, which would be intended for the patient while the patient is not conscious. And, not knowing any better, such a bystander may think that such a shock could harm the patient. The bystander's way to protect the patient could be by actuating cancel switch 377, exactly as the warning could have instructed to do to prevent the impending shock. For such cases, the WCD system may further include speaker system 374. Speaker system 374 can output a transmitted sound that communicates that the actuation of cancel switch 377 will be ignored. It can further advise a bystander to stand back, ask them to speak, and so on.

FIG. 26 shows a flowchart 2600 for describing methods according to embodiments. The methods of flowchart 2600 may also be practiced by embodiments described in this document.

According to an operation 2610, motion data is generated, for example by a motion detector. According to another operation 2620, a physiological input is rendered from a patient physiological signal. The physiological input may be rendered by a measurement circuit. According to another, optional operation 2630, it can be determined whether or not a shock condition is met. The determination may be computed by a processor from the physiological input, for example according to criteria. If the shock condition is not met, then flowchart 2600 may be exited.

If, at operation 2630, it is determined that the shock condition is met then, according to another, optional operation 2640, a warning may be output about an impending shock that will be administered to the patient. The warning may include words to the patient to actuate a cancel switch to prevent the shock, which is a procedure that the patient has preferably been trained upon, when first fitted with the WCD system.

According to another operation 2650, it can be sensed whether a cancel switch is actuated. In the context of flowchart 2600, this sensing takes place when the shock condition is determined to be met at operation 2630. In some embodiments, the warning of operation 2640 may permit only a fixed time interval to actuate the cancel switch. In these embodiments, operation 2650 is deemed to have been answered as "no" if that time interval passes without actuation.

If, at operation 2650, it is determined that the cancel switch has not been actuated, then according to another operation 2680, the discharge circuit can be controlled to discharge the electrical charge through the patient responsive to the shock condition being met.

If, at operation 2650, it is determined that the cancel switch has been actuated then, according to another operation 2660, it can be determined whether or not the motion data generated at operation 2610 meets a spuriousness threshold. The spuriousness threshold can be defined, for example in terms of a score or a condition that is assigned to aspects of the motion data, as per the above. If the spuriousness threshold is not met, then the actuation of the cancel switch is deemed legitimate, and flowchart 2600 may be exited.

If, at operation 2660, it is determined that the spuriousness threshold is met then, according to another, optional operation 2670, a transmitted sound may be output, for example via a speaker system. The transmitted sound may communicate that the actuation of the cancel switch will be ignored, and the impending shock will be delivered anyway. It may also communicate additional items, such as a warning to stand back, a request for a bystander to speak, etc. The execution may again proceed to operation 2680, perhaps after first giving more time, asking for another actuation, testing for spuriousness in a different way, and so on. Operation 2680 can thus take place while the support structure is worn by the patient, even though the cancel switch is actuated in this context, since the motion data met the spuriousness threshold.

Another example is now described for ensuring that the cancel switch has been actuated only by a person authorized in advance. Briefly, a WCD system may authenticate a person actuating the cancel switch. More particularly, the cancel switch can be configured to be actuated in conjunction with receiving a correct validation input, so as to authenticate the person who is entering the validation input. An example is now described.

In some embodiments, a WCD system may include support structure 370, energy storage module 350, measurement circuit 320, processor 330, discharge circuit 355, and cancel switch 377 from collection 302 of FIG. 3. The cancel switch can be further configured to be actuated in conjunction with receiving a validation input entered by a person, which may be part of user interface 373. The person can be, of course, the patient, plus perhaps a possible preauthorized anticipated bystander. If cancel switch 377 is actuated, it may prevent an electrical charge from being discharged even if a shock condition is met, but the electrical charge can be so prevented only if a validation input has indeed been entered, and the entered validation input meets a validity criterion.

The validation input may be received in a number of ways. In some embodiments, the cancel switch is made so that actuating it involves directly also entering the validation input. For example, the cancel switch may include a keyboard, and actuating the cancel switch in conjunction with receiving the validation input would accordingly include entering a code in the keyboard, such as a password, a PIN, etc. The keyboard can be made by physical keys, by a touchscreen, and so on. Or, the cancel switch may include a fingerprint reader, and actuating the cancel switch in conjunction with receiving the validation input can include scanning a fingerprint of a preapproved user in the fingerprint reader. The preapproved user can be the patient, specific anticipated bystanders, whether they know the patient or whether they have advance clearance to render appropriate aid to this patient, etc.

In other embodiments, a validation input device is provided that is distinct from the cancel switch. This validation input device can be configured to receive the validation input before or after the cancel switch is actuated. Similarly, and as per the above, this validation input device can include a keyboard, a fingerprint reader, etc.

In yet other embodiments, the validation input may be spoken, for example by the patient. More particularly, the WCD system may include microphone 376, which is configured to sense an ambient sound. In such cases, receiving the validation input may include sensing an ambient sound, and the validity criterion can be is that the sensed sound includes one or more preset validation words, such as "OK", "I AM OK", "DO NOT SHOCK ME", a code such as "1-2-3-4", the last four digits of the patient's social security number, and so on.

Thus, actuating cancel switch 377 may be deemed invalid if not entered with the appropriate validation input. For such cases, the WCD system may further include speaker system 374. Speaker system 374 can output a transmitted sound that communicates that the actuation of cancel switch 377 will be ignored. It can further advise a bystander to stand back, ask them to speak, and so on.

FIG. 27 shows a flowchart 2700 for describing methods according to embodiments. The methods of flowchart 2700 may also be practiced by embodiments described in this document.

According to an operation 2720, a physiological input is rendered from a patient physiological signal. The physiological input may be rendered by a measurement circuit. According to another, optional operation 2730, it can be determined whether a shock condition is met. The determination may be computed by a processor from the physiological input, for example according to criteria. If the shock condition is not met, then flowchart 2700 may be exited.

If, at operation 2730, it is determined that the shock condition is met then, according to another, optional operation 2740, a warning may be output about an impending shock that will be administered to the patient. The warning may include words to the patient to actuate a cancel switch to prevent the shock, which is a procedure that the patient has preferably been trained upon, when first fitted with the WCD system.

According to another operation 2750, it can be sensed whether or not a cancel switch is actuated, in conjunction with receiving a validation input entered by a person. In the context of flowchart 2700, this sensing takes place when the shock condition is determined to be met at operation 2730. In some embodiments, the warning of operation 2740 may permit only a fixed time interval to actuate the cancel switch. In these embodiments, operation 2750 is deemed to have been answered as "no" if that time interval passes without actuation. If the cancel switch has been actuated, a validation input may then be requested to be entered, and perhaps the time interval can be extended somewhat.

If, at operation 2750, it is determined that the cancel switch has not been actuated, then according to another operation 2780, the discharge circuit can be controlled to discharge the electrical charge through the patient responsive to the shock condition being met.

If, at operation 2750, it is determined that the cancel switch has been actuated then, according to another operation 2760, it can be determined whether or not the validation input received at operation 2750 meets a validity criterion, for example if a code matches, and so on. If the validity criterion is met, then flowchart 2700 may be exited, since the cancel switch is sensed to have been actuated in conjunction with receiving an entered validation input that meets the validity criterion.

If, at operation 2760, it is determined that the validity criterion is not met then, according to another, optional operation 2770, a transmitted sound may be output, for example via a speaker system. The transmitted sound may communicate that the actuation of the cancel switch will be ignored, and the impending shock will be delivered anyway. It may also communicate additional items, such as a warning to stand back, a request to speak, an offer for a validation input to be entered again, etc.

The execution may again proceed to operation 2780. This may take place while the support structure is worn by the patient.

In embodiments, a WCD system may include a user interface that a bystander can operate. Briefly, a WCD system may authenticate a person accessing all or portions of the user interface, so as to restrict access only to preauthorized people. An example is now described.

In some embodiments, a WCD system (not shown separately) may include support structure 370, energy storage module 350, discharge circuit 355, and user interface 373 from collection 302 of FIG. 3. User interface 373 can be configured to receive usage inputs from a bystander or the patient, for example via speaker system 374, microphone 376, and/or inputting mechanism 379. Inputting mechanism 379 may also include a fingerprint reader. User interface 373 can be further configured to perform acts responsive to the usage inputs, such as display items on screen 375, generate sounds by speaker system 374, communicate with a remote care giver, etc.

User interface 373 can be further configured to receive a validation input, which can be accomplished in a number of ways. For example, inputting mechanism 379 may include a keyboard, and the corresponding validation input can be a personal identification code. Or, inputting mechanism 379 may include a fingerprint reader, and the corresponding validation input can include scanning a fingerprint of a preapproved user in the fingerprint reader. In some of these embodiments, therefore, at least one of the acts is performed only if the validation input meets a validity criterion. This way only a person with proper authorization may access one or more of the features, or all the features. Such a person can be, the patient, and/or possible specific anticipated bystanders, whether they know the patient or whether they have advance clearance to render appropriate aid to this patient.

In some embodiments, the speaker system is configured to output a transmitted sound requesting that the validation input be entered. This request would be a reminder to someone who would have training, but might forget it at the critical time.

In some embodiments, the speaker system is configured to output a transmitted sound having substantially periodic contents, which are designed to assist a bystander to perform CPR chest compressions on the patient. These can be as described for contents 1973. In addition, an aspect of the contents can be different, depending on the usage input, which would be depending on the anticipated qualification of the bystander. The aspect can be a frequency of the contents, or a number of how many tones are in a sequence for the compressions, a number of how many sequences of compressions between shocks, a total number of tones before the next discharge, whether or not to perform ventilations, etc.

Figure 28:
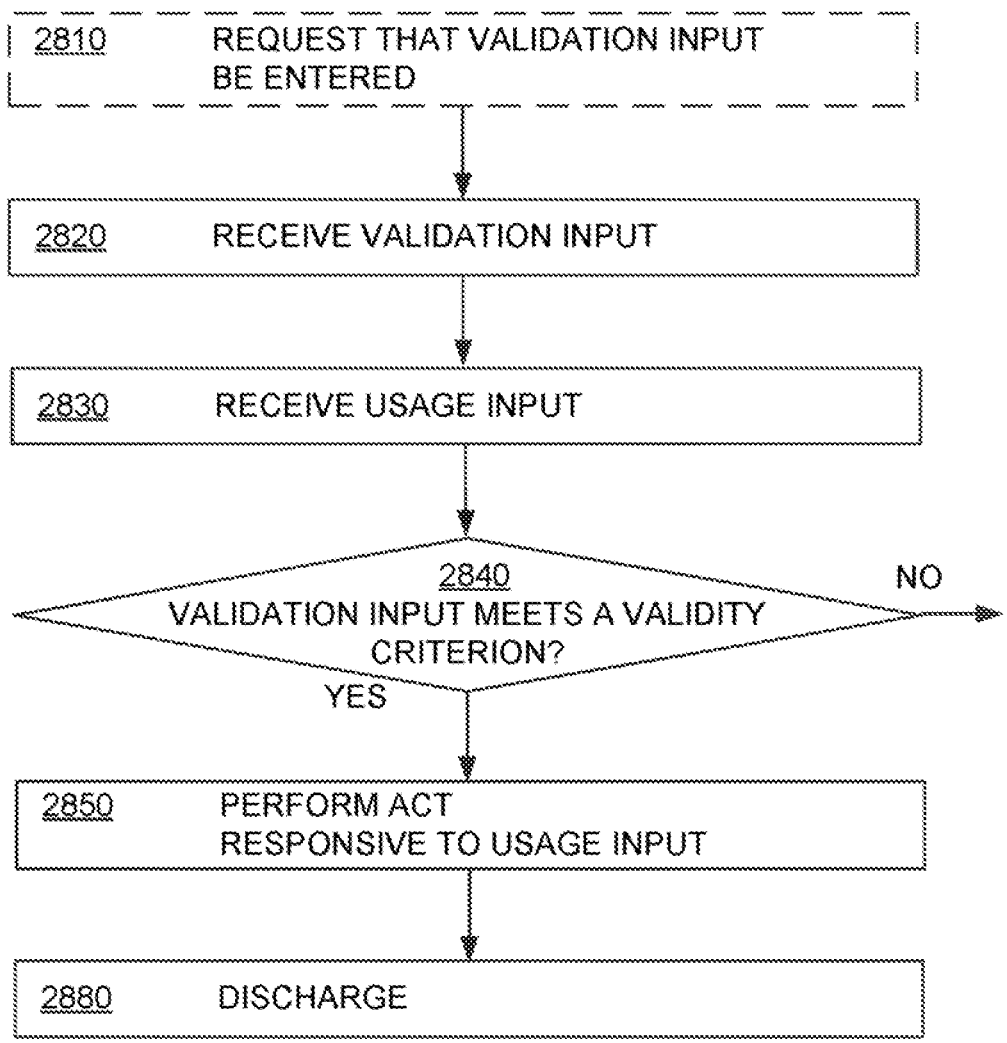
FIG. 28 is a flowchart for illustrating sample methods according to embodiments.

FIG. 28 shows a flowchart 2800 for describing methods according to embodiments. The methods of flowchart 2800 may also be practiced by embodiments described in this document.

According to an optional operation 2810, it may be requested that a validation input be entered. The request may be made by the interface, and be audible, displayed, etc.

According to another operation 2820, a validation input may be received. The validation input may be received in the user interface, and responsive to the request of operation 2810.

According to another operation 2830, a usage input may be received. The usage input may be received in the user interface, and be of the type that a bystander enters to control a WCD system. Operation 2830 may be performed before or after operation 2820.

According to another operation 2840, it is inquired whether the validation input received in operation 2830 meets a validity criterion. If not, then flowchart 2820 may be exited.

According to another operation 2850, an act is performed response to the received usage input. There can be any number of acts, such as opening a communication channel, turning off, switching modes, issuing CPR prompts, switching to manual defibrillation, etc. In this context, the act is performed if the validation input meets the validity criterion, else it is not performed.

According to another operation 2880, the discharge circuit can be controlled to discharge the electrical charge through the patient, while the support structure is worn by the patient.

In the methods described above, each operation can be performed as an affirmative step of doing, or causing to happen, what is written that can take place. Such doing or causing to happen can be by the whole system or device, or just one or more components of it. In addition, the order of operations is not constrained to what is shown, and different orders may be possible according to different embodiments. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily the present invention. Plus, any reference to any prior art in this description is not, and should not be taken as, an acknowledgement or any form of suggestion that this prior art forms parts of the common general knowledge in any country.

This description includes one or more examples, but that does not limit how the invention may be practiced. Indeed, examples or embodiments of the invention may be practiced according to what is described, or yet differently, and also in conjunction with other present or future technologies. Other embodiments include combinations and sub-combinations of features described herein, including for example, embodiments that are equivalent to: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in any number of ways, as will be apparent to a person skilled in the art after reviewing the present disclosure, beyond any examples shown in this document.

The following claims define certain combinations and subcombinations of elements, features and steps or operations, which are regarded as novel and non-obvious. Additional claims for other such combinations and subcombinations may be presented in this or a related document.

The embodiments of the invention in which an exclusive property or privilege is claimed are defined as follows:

1. A wearable cardiac defibrillator (WCD) system, comprising:
   a support structure configured to be worn by a patient;
   a power source;
   an energy storage module configured to receive an electrical charge from the power source, and to store the received electrical charge;
   a measurement circuit configured to render a physiological input from a patient physiological signal;
   a motion sensor configured to measure motion data of a patient;
   a location sensor configured to measure location data indicative of a location of the patient wherein the location data is used to inform the determination of whether the shock condition has been met;
   a processor configured to determine from the physiological input whether or not a shock condition is met;
   a discharge circuit configured to be coupled to the energy storage module and configured to discharge the stored electrical charge through the patient while the support structure is worn by the patient when the shock condition is met;
   a cancel switch configured to be actuated in conjunction with receiving a validation input entered by a person, in which when the cancel switch is sensed to have been actuated it prevents the electrical charge from being discharged even when the shock condition is met, but the electrical charge is so prevented only when the entered validation input meets a validity criterion and in response to the motion data of the patient exceeds a spuriousness threshold, the actuation of the cancel switch is ignored, and an electrical shock is discharged.

2. The WCD system of claim 1, in which the cancel switch includes a keyboard, and
   actuating the cancel switch in conjunction with receiving the validation input includes entering a code in the keyboard.

3. The WCD system of claim 1, in which the cancel switch includes a fingerprint reader, and
   actuating the cancel switch in conjunction with receiving the validation input includes scanning a fingerprint of a preapproved user in the fingerprint reader.

4. The WCD system of claim 1, further comprising:
   a validation input device distinct from the cancel switch, and configured to receive the validation input.

5. The WCD system of claim 4, in which the validation input device includes a keyboard, and the validation input includes a code.

6. The WCD system of claim 4, in which the validation input device includes a fingerprint reader, and
   the validation input includes scanning a fingerprint of a preapproved user in the fingerprint reader.

7. The WCD system of claim 1, further comprising:
   a microphone coupled to the support structure and configured to sense an ambient sound, and
   in which receiving the validation input includes sensing an ambient sound, and the validity criterion is that the sensed sound includes one or more preset validation words.

8. The WCD system of claim 1, further comprising:
   a speaker system coupled to the support structure and configured to output a transmitted sound that communicates that the actuation of the cancel switch will be ignored.

9. The WCD of claim 1, wherein the location sensor is coupled to the support structure.

10. The method of claim 1, wherein the location data comprises a change of location data.

11. The WCD system of claim 1, wherein the location data is at least partially based on GPS data.

12. A method for a wearable cardiac defibrillator (WCD) system, the WCD system including a support structure configured to be worn by a patient, a power source, an energy storage module configured to receive an electrical charge from the power source, and to store the received electrical charge, a measurement circuit configured to render a physiological input from a patient physiological signal, a processor configured to determine from the physiological input whether or not a shock condition is met, a discharge circuit configured to be coupled to the energy storage module and configured to discharge the electrical charge through the patient responsive to a determination that the shock condition is met, a location sensor configured to measure location data indicative of a location of the patient, a cancel switch configured to prevent the discharge circuit from discharging the electrical charge responsive to the determination that the shock condition is met, and a validation input device,
   the method comprising:
   rendering, by the measurement circuit, a physiological input from a patient physiological signal;
   determining from the physiological input and the location data that the shock condition is met; sensing, when the shock condition is determined to be met, that the cancel switch is actuated in conjunction with receiving a validation input entered by a person; and controlling the discharge circuit to discharge the electrical charge through the patient while the support structure is worn by the patient responsive to the shock condition being met, except that the discharge circuit is controlled to not so discharge in response to the cancel switch being sensed to have been actuated in conjunction with receiving an entered validation input, and the entered validation input meets a validity criterion; and determining when motion data measured by a motion sensor exceeds a spuriousness threshold, and when it is determined it does, controlling the discharge circuit to discharge the electrical charge through the patient.

13. The method of claim 12, in which the WCD system further includes a microphone coupled to the support structure, and further comprising: sensing an ambient sound as the validation input, and in which the validity criterion is that the sensed sound includes one or more preset validation words.

14. The method of claim 12, in which the WCD system further includes a speaker system coupled to the support structure, and further comprising: outputting, via the speaker system, a transmitted sound that communicates that the actuation of the cancel switch will be ignored.

15. A wearable cardiac defibrillator (WCD) system, comprising:

a support structure configured to be worn by a patient;

a power source;

an energy storage module configured to receive an electrical charge from the power source, and to store the received electrical charge;

a discharge circuit configured to be coupled to the energy storage module and configured to discharge the electrical charge through the patient while the support structure is worn by the patient;

a motion sensor configured to measure motion data of the patient;

a location sensor configured to measure location data indicative of a location of the patient, wherein the location data is used to inform the determination of whether the shock condition has been met;

a user interface configured to be coupled to the support structure and to receive a usage input from a bystander and to perform an act responsive to the usage input, the user interface further configured to receive a validation input, in which the act is performed responsive to the validation input meeting a validity criterion; and wherein when the motion data of the patient exceeds a spuriousness threshold, the actuation of a cancel switch is ignored, and an electrical shock is discharged.

16. The WCD system of claim 15, in which the user interface includes a keyboard, and the validation input includes a code.

17. The WCD system of claim 15, in which the user interface includes a fingerprint reader, and the validation input includes scanning a fingerprint of a preapproved user in the fingerprint reader.

18. The WCD system of claim 15, in which the user interface includes a speaker system configured to output a transmitted sound requesting that the validation input be entered.

19. The WCD system of claim 15, in which the user interface includes a speaker system configured to output a transmitted sound having substantially periodic contents designed to assist a bystander to perform CPR chest compressions on the patient, in which an aspect of the contents is different depending on the usage input.

20. The WCD system of claim 19, in which the aspect is a total number of tones before the next discharge.

* * * * *